(12) United States Patent
Castillo et al.

(10) Patent No.: US 7,094,580 B2
(45) Date of Patent: Aug. 22, 2006

(54) METHODS FOR PRODUCING PURE PERLECAN AND OTHER HEPARAN SULFATE PROTEOGLYCANS

(75) Inventors: Gerardo Castillo, Seattle, WA (US); Alan D. Snow, Lynnwood, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 10/323,323

(22) Filed: Dec. 18, 2002

(65) Prior Publication Data
US 2003/0153734 A1     Aug. 14, 2003

Related U.S. Application Data

(63) Continuation of application No. 09/698,518, filed on Oct. 26, 2000, now abandoned, which is a continuation of application No. 09/036,492, filed on Mar. 6, 1998, now abandoned.

(60) Provisional application No. 60/038,613, filed on Mar. 6, 1997.

(51) Int. Cl.
  *C12P 19/00* (2006.01)
  *C12N 5/00* (2006.01)
  *C07K 14/00* (2006.01)
  *C07K 17/00* (2006.01)
  *C07K 9/00* (2006.01)

(52) U.S. Cl. .......... 435/72; 435/84; 435/101; 435/130; 435/325; 530/300; 530/305; 530/322; 530/336; 530/344; 530/350; 530/354; 530/355; 530/356; 530/357

(58) Field of Classification Search .......... 435/72, 435/84, 101, 130, 325; 530/300, 305, 322, 530/336, 344, 350, 354, 355, 356, 357
See application file for complete search history.

(56) References Cited

OTHER PUBLICATIONS

Castillo et al. J. Biochem. 120, 433-444, 1996.*
Yurchenco et al. Methods of Enzymology, vol. 245, pp. 489-518, 1994.*
Rip et al. Biochem. J. vol. 288, pp. 1005-1010, 1992.*
Oda et al. "Purification and characterization of perlecan fragment in urine of end-stage renal failure patients" Clinica Chimica Acta 255 (1996) 119-132.*

* cited by examiner

*Primary Examiner*—Jezia Riley
(74) *Attorney, Agent, or Firm*—Patrick M. Dwyer

(57) ABSTRACT

A method of perlecan isolation (from the EHS tumor) which produces "clean" (i.e. substantially "pure") perlecan is disclosed. Clean perlecan is thus produced in sufficient quantities for use in a number of different in vitro and in vivo assays. In addition, this isolation method exploits a newly discovered aggregating property of a ~220 kDa heparan sulfate proteoglycan (HSPG) observed during gel filtration chromatography, which allows it to be effectively separated from non-aggregating perlecan. The method employs specific cation exchange, anion exchange, molecular sieve chromatography and immobilized GAG affinity chromatography. It is demonstrated that there are no other contaminating proteins in the perlecan and HSPG preparations, and that the perlecan core protein is intact. Improved, clean perlecan based, rodent models of fibrillar amyloid protein deposition, accumulation and/or persistence in tissues are disclosed.

13 Claims, 5 Drawing Sheets

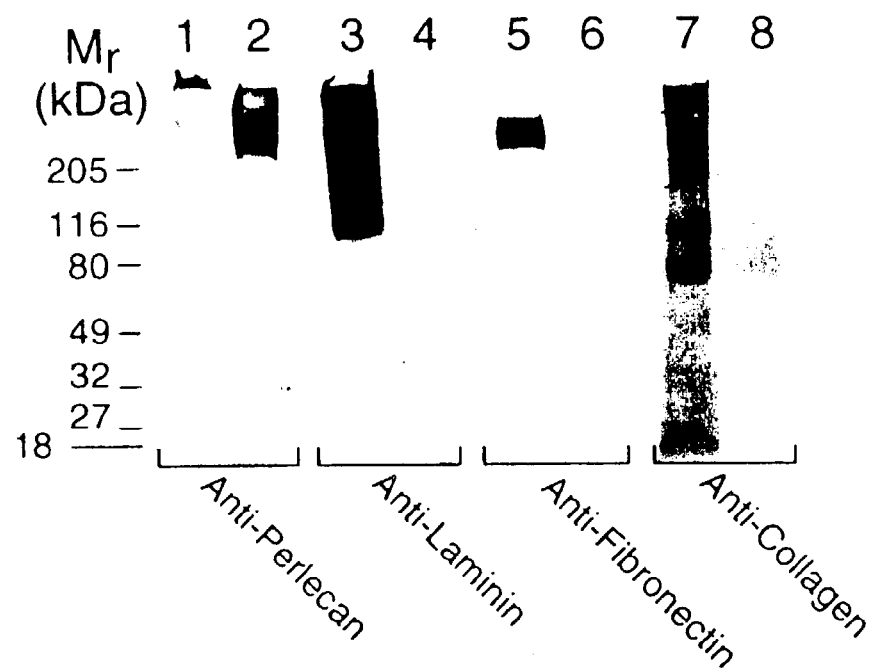
FIGURE 6
        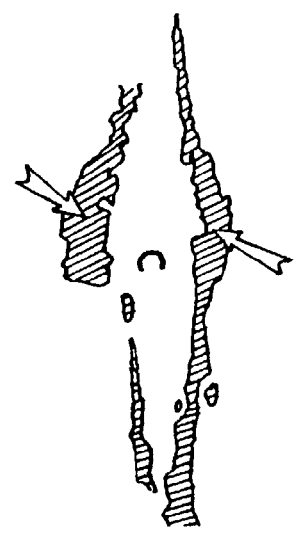
FIGURE 8a          FIGURE 8b          FIGURE 8c

METHODS FOR PRODUCING PURE PERLECAN AND OTHER HEPARAN SULFATE PROTEOGLYCANS

This application is a Continuation of Ser. No. 09/698,518 filed Oct. 26, 2000 now abandoned which is a Continuation of Ser. No. 09/036,492 filed Mar. 6, 1998, now abandoned, which claimed priority to provisional application 60/038,613 filed Mar. 6, 1997.

TECHNICAL FIELD

The invention relates to methods for producing pure perlecan and other heparan sulfate proteoglycans; more particularly, it relates to methods for isolating and purifying perlecan and other heparan sulfate proteoglycans from tissue extracts by means of column chromatography; moreover, it relates to the pure perlecan and other heparan sulfate proteoglycans produced by these methods and to assays and animal models employing these pure substances.

BACKGROUND OF THE INVENTION

Perlecan is a specific heparan sulfate proteoglycan (HSPG) and a common constituent of all amyloid deposits regardless of the specific amyloid protein involved. Perlecan is believed to play primary roles in the pathogenesis of amyloidosis and contributes to the formation, deposition, accumulation and/or persistence of amyloid in a variety of tissues and in different clinical settings.

However, perlecan is an extremely difficult macromolecule to isolate in pure form, especially in substantial quantities, due in part to perlecan's inherent ability to interact with a number of different proteins and macromolecules. The most commonly utilized extract source for isolation of perlecan is the Engelbreth-Holm-Swarm (EHS) tumor which is routinely grown in the hind legs of mice. However, major problems still exist with trying to obtain "clean" perlecan from this basement membrane producing tumor, especially when using known methods of isolation. These problems include: a) contamination by other proteins and/or basement membrane components of the EHS tumor including laminin, fibronectin and type IV collagen which all tend to interact with perlecan, b) contamination due to the presence of free glycosaminoglycan (GAG) chains, and c) degradation of the perlecan core protein.

Thus, there is a need in the art to develop effective new ways to isolate perlecan in high yield and of high quality (i.e. "clean" or substantially "pure" perlecan) in order to use this product for a number of important biological assays which have impact on a number of major human diseases including Alzheimer's disease, Down's syndrome, type II diabetes, certain forms of cancer and inflammatory disorders. All of these latter diseases involve amyloid accumulation and persistence, and involve perlecan and related HSPGs in the pathogenesis. Isolation of perlecan for use in further understanding perlecan's role in the pathogenesis of these major human disorders and for the eventual identification of new therapeutics will be of tremendous benefit.

DISCLOSURE OF THE INVENTION

Summary of the Invention

The present invention describes methods of perlecan isolation and purification which produce "clean" perlecan, and do so in sufficient quantities for effective use in a number of different in vitro and in vivo assays. In addition, this isolation method does not require cesium chloride (or other density gradient) centrifugation and exploits a newly discovered aggregating property of a ~220 kilodalton (kDa) heparan sulfate proteoglycan (HSPG) observed during gel filtration (i.e. molecular sieve) chromatography, which allows it to also be effectively isolated separately from non-aggregating perlecan.

In these methods, 50–200 grams of EHS tumor are routinely extracted using 4M guanidine-HCl, followed by specific cation exchange, anion exchange and/or molecular sieve chromatography. SDS-PAGE analysis (before and after digestion with heparitinase/heparinase or nitrous acid) followed by staining with silver, demonstrates no other contaminating proteins in the perlecan preparations. Western blots using a specific perlecan core protein antibody (HK-102) following heparitinase digestion show a characteristic doublet at 400 and 360 kDa indicative of intact perlecan core protein. Absence of contamination by other basement membrane components produced by the EHS tumor is confirmed by absence of immunoreactive bands on Western blots using antibodies against laminin, fibronectin or type IV collagen.

The present invention describes detailed isolation and characterization of perlecan and a ~220 kDa HSPG from the EHS tumor to ensure quantity production of perlecan and the ~220 kDa HSPG of the highest quality, and to maximize the potential effects of these products using in vitro assays, and in a rodent model of fibrillar beta-amyloid protein deposition, accumulation and/or persistence in brain tissue. In addition, the methodology describes the unique isolation of a ~220 kDa HSPG from the EHS tumor. Lastly, several aspects of the isolation methodology described, including the use of anionic resins (i.e. cationic exchange resins) and immobilized glycosaminoglycans (GAGs), can also be applied, as for instance following conventional extraction techniques, to obtain preparations of other "clean" proteoglycans (PGs) from different tissue, organ, tumor or cell culture sources.

Features of the Invention

Perlecan is a specific HSPG which is present on all basement membranes (Dziadek et al., *EMBO J.* 4:905–912, 1985; Kato et al., *J. Cell Biol.* 106:2203–2210, 1988; Murdoch et al., *J. Histochem. Cytochem.* 42:239–249, 1988). Perlecan is believed to play fundamental roles in the pathogenesis of Alzheimer's disease (AD) amyloidosis, as well as in other types of central nervous system and systemic amyloidoses (reviewed in Snow and Wight, *Neurobiol. Aging* 10:481–497, 1989). Perlecan can be routinely isolated from the EHS mouse tumor. However, it is extremely difficult to isolate perlecan in "pure" form and in sufficient quantities due to perlecan's inherent ability to interact with other basement membrane components (i.e. Laminin, fibronectin and/or type IV collagen) which are also produced by the EHS tumor. This invention relates to detailed methodology that allows one to isolate perlecan in relatively "pure" or "clean" form and in sufficient quantities for use in a number of different and relevant in vitro and in vivo assays. Some of the work disclosed here has been reported by G M Castillo, J A Cummings, C Ngo, W Yang and A D Snow in a manuscript entitled Novel Purification and Detailed Characterization of Perlecan Isolated from the Engelbreth-Holm-Swarm Tumor for Use in an Animal Model of Fibrillar Aβ Amyloid Persistence in Brain, in *J. Biochem.* 120:433–444, 1996, the substance of which is hereby incorporated by reference.

A primary object of the present invention is to provide methods for the isolation of intact and "clean" (i.e. substantially "pure") perlecan which does not contain contaminating proteins or other macromolecules. The terms "clean" "substantially pure" and/or "free (of contaminants)" are used herein to refer to isolated perlecan or HSPGs that contain less than 1% (and preferably 0.1% or less) by weight of contaminating proteins, other macromolecules or DNA.

Yet another object of the present invention is to provide methods for the isolation of a quantity of intact and "clean" HSPG such as perlecan which preferably contains substantially no (less than 1% and preferably less than or equal to 0.1%) contaminating basement membrane components including laminin, fibronectin, or type IV collagen.

Yet another object of the present invention is to provide methods for the isolation of a quantity of intact and "clean" HSPG such as perlecan which preferably contains substantially no (less than 1% and preferably less than or equal to 0.1%) of free glycosaminoglycan (GAG) chains.

Yet another object of the present invention is to provide methods for the isolation of a quantity of intact and "clean" HSPG such as perlecan which preferably contains substantially no (less than 1% and preferably less than or equal to 0.1%) of potential contaminating DNA.

Yet another object of the present invention is to provide methods for the consistent production of "clean" perlecan in sufficient quantities for use in a number of different and relevant in vitro and in vivo biological assays.

Yet another object of the present invention is to provide like methods to isolate other proteoglycans from human and animal tissues or cell culture, such that the isolated PGs are essentially "free" of contaminating laminin, fibronectin, type IV collagen and/or other matrix proteins (i.e. those proteins that normally interact with proteoglycans).

Yet another object of the present invention is to provide methods to remove PG-associated proteins or macromolecules in order to obtain "clean" or substantially "pure" PG preparations.

Yet another object of the present invention is to provide methods for the use of immobilized GAGs to remove PG-associated proteins or macromolecules in order to obtain "clean" or substantially "pure" PG preparations.

Yet another object of the present invention is to provide methods for the use of cation exchange resins to remove PG-associated proteins or macromolecules in order to obtain "clean" or substantially "pure" PG preparations.

Another aspect of the present invention is to use "clean" perlecan and/or ~220 kDa HSPG (i.e. perlecan and/or ~220 kDa HSPG produced by one or more methods of the invention) to establish new therapeutic methods and diagnostic applications for the amyloid diseases, methods otherwise impractical with conventionally prepared perlecan or HSPG.

The amyloid diseases referred to herein include, but are not limited to, the amyloid associated with Alzheimer's disease and Down's syndrome (wherein the specific amyloid is referred to as beta-amyloid protein or Aβ), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prior diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as beta$_2$-microglobulin amyloid), the amyloid associated with senile cardiac amyloid and Familial Amyloidotic Polyneuropathy (wherein the specific amyloid is referred to as transthyretin or prealbumin), and the amyloid associated with endocrine tumors such as medullary carcinoma of the thyroid (wherein the specific amyloid is referred to as variants of procalcitonin).

Another aspect of the present invention is to use "clean" perlecan and/or ~220 kDa HSPG to produce new polyclonal and/or monoclonal antibodies of a previously unattainable purity and integrity which can then be employed in a number of in vitro assays to specifically detect perlecan, perlecan derived-fragments, the ~220 kDa HSPG and ~220 kDa HSPG-derived fragments in human tissues and/or biological fluids. Polyclonal or monoclonal antibodies made specifically against "clean" perlecan, a protein core fragment of "clean" perlecan (which interacts with specific amyloid proteins), or the ~220 kDa HSPG can be put to a most effective use to detect and quantify amyloid disease specific perlecan or ~220 kDa HSPG fragments in human tissues and/or biological fluids, and to a previously unattainable degree of precision. These antibodies can be made by administering the "clean" perlecan or the ~220 kDa HSPG in antigenic form to a suitable host. Polyclonal or monoclonal antibodies may be prepared by standard techniques known to those skilled in the art.

Another object of the present invention is to use perlecan or ~220 kDa HSPG-specific antibodies referred to above for the detection and specific localization of perlecan, the ~220 kDa HSPG or their fragments in human tissues, cells, and/or cell culture using standard immunohistochemical techniques, known to those skilled in the art.

Yet another aspect of the present invention is to use antibodies recognizing perlecan, ~220 kDa HSPG, or fragments thereof, for in vivo labeling; for example, with a radionucleotide, for radioimaging to be utilized for in vivo diagnosis, and/or for in vitro diagnosis.

Another object of the present invention is to use clean perlecan and/or perlecan-derived peptides or fragments for use in in vitro assays to detect perlecan autoantibodies in human biological fluids. Specific assay systems can be utilized to not only detect the presence of perlecan autoantibodies in biological fluids, but also to monitor the progression of disease by following elevation or diminution of perlecan autoantibody levels.

Another aspect of the invention is to use clean perlecan, perlecan fragments, perlecan-derived peptides, ~220 kDa HSPG or fragments thereof, to generate antibodies and/or molecular biology probes for the detection of perlecan or the ~220 kDa HSPG in human tissues in the amyloid diseases.

Yet another aspect of the present invention is to utilize "clean" perlecan or ~220 kDa HSPG products for the establishment of new animal models for the deposition, accumulation and/or persistence of fibrillar Aβ amyloid in brain as observed in Alzheimer's disease and Down's syndrome. These new animal models can be used to effectively screen and identify new therapeutic agents that target fibrillar Aβ amyloid formation, deposition, accumulation and/or persistence in brain.

Yet another aspect of the present invention is to provide new animal models for the production, deposition, accumulation and/or persistence of fibrillar amyloid as observed in each of the other amyloidoses, by employing the "clean" perlecan of the invention. This includes, but is not limited to, the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as beta$_2$-microglobulin amyloid), the amyloid associated with senile cardiac amyloid and Familial Amyloidotic Polyneuropathy (wherein the specific amyloid is referred to as transthyretin or prealbumin), and the amyloid associated with endocrine tumors such as medullary carcinoma of the thyroid (wherein the specific amyloid is referred to as variants of procalcitonin). These new animal models can also be used for the evaluation of candidate drugs and therapies for the prevention and treatment of the amyloidoses as referred to above.

In a particular aspect of the invention there is a method of preparation of substantially pure proteoglycan from an extract source, with the method using some or all of the following steps: a) isolation of an extracted proteoglycan by molecular sieve column chromatography, b) cation exchange column chromatography, c) anion exchange column chromatography, and d) chromatography using a column containing immobilized glycosaminoglycans. The proteoglycan referred to is advantageously perlecan, but can be the ~220 kDa HSPG (aggregating or not), or fragments thereof, and the preferred though not exclusive extract source is Engelbreth-Holm-Swarm tumor tissue.

The isolation by molecular sieve column chromatography employs a Sephacryl S-400 column; the isolation by cation exchange column chromatography employs a Sulphopropyl Sepharose column; the isolation by anion exchange column chromatography employs a DEAE-Sephacel column; the isolation by a molecular sieve column employs a second column in the form of a Sephacryl S-1000 column; the isolation by a column containing immobilized glycosaminoglycans employs a heparin-Sepharose column. In each variation of the method, isolation proceeds to a level of contaminating proteins, proteoglycans or macromolecules of less than 1%, or to a level of contamination by DNA of less than 1%, and preferably proceeds in any case to a level of contaminating proteins, proteoglycans or macromolecules of less than or equal to 0.1%.

Another aspect of the invention is the clean perlecan produced by the method of the invention, having a level of contaminating proteins, proteoglycans, macromolecules or DNA of less than 1%. Another aspect is a method of making an antibody, with the method producing antibodies from the clean perlecan. The making of the antibody includes the step of production of at least one type of antibody selected from the group of antibody types consisting of polyclonal, monoclonal, and chimeric antibodies and anti-idiotypic antibodies.

There is also a disclosed a method to diagnose a disease or a susceptibility to a disease related to the levels of perlecan, perlecan-derived protein or glycosaminoglycans fragments, ~220 kDa HSPG, or ~220 kDa HSPG-derived protein or glycosaminoglycans fragments, the method comprising determining levels of perlecan, a particular perlecan-derived fragment, or the ~220 kDa HSPG, or ~220 kDa derived fragment in a sample, whereby the levels are indicative of the presence of a disease, susceptibility to a disease, or progression of said disease, such as an amyloid disease. This method can advantageously include the step of radiolabeling the antibodies for radioimaging or in vivo diagnosis for detection of perlecan, perlecan-derived protein or glycosaminoglycans fragments, ~220 kDa HSPG, or ~220 kDa HSPG-derived protein or glycosaminoglycan fragments.

There is also disclosed a method for detection and quantification of perlecan and perlecan-derived fragments in biological fluids comprising a) allowing a first clean perlecan or perlecan-derived fragment antibody to bind to microtiter wells for a sufficient time to allow said binding, b) adding a quantity of biological fluid to the microtiter wells, c) incubating the biological fluid for sufficient time to allow binding of any perlecan or perlecan-derived fragment in the biological fluid to the first antibody on the microtiter wells, d) adding a second labeled antibody to the microtiter wells wherein the second labeled antibody is against perlecan or perlecan-derived fragment, but which is against a different epitope than the first antibody, and allowing the second antibody to bind to any perlecan or perlecan-derived fragment captured by the first antibody, and e) detecting bound materials using an appropriate substrate or label.

There is also disclosed a method for detection and quantification of perlecan autoantibodies in biological fluids comprising a) allowing clean perlecan or a fragment thereof to bind to microtiter wells for a sufficient time to allow said binding, b) adding a quantity of biological fluid to the microtiter wells, c) incubating the biological fluid for sufficient time to allow binding of any perlecan autoantibody in the biological fluid to the clean perlecan or a fragment thereof on the microtiter wells, d) adding a labeled antibody to the microtiter wells wherein the labeled antibody is against human immunoglobulins and allowing the antibody to bind to any perlecan autoantibody captured by the perlecan or a fragment thereof, and e) detecting bound materials using an appropriate substrate or label.

In any of the methods of the invention, the biological fluids may be blood, plasma, serum, cerebrospinal fluid, sputum, saliva, urine and stool or the like.

There is also disclosed a method for the treatment of a patient having an identified clinical need to interfere with the pathological effects of amyloid, the method comprising administrating to the patient a therapeutically effective amount of clean perlecan, or a protein or glycosaminoglycan fragment thereof, where the amyloid disease is Alzheimer's disease.

There is also disclosed a method for producing an animal model of amyloid diseases comprising a) injecting or infusing clean perlecan, the ~220 kDa HSPG, or fragments thereof, in combination with the appropriate amyloid protein into a given tissue or organ of a non-human mammal, and b) allowing sufficient time for the amyloid protein plus perlecan or the ~220 kDa HSPG to be co-deposited in said tissue or organ, c) detecting the amyloid deposit in said organ in tissue using standard staining techniques for fibrillar amyloid. In this method the amyloid disease may be Alzheimer's disease and the appropriate amyloid protein may be the beta-amyloid protein (A$\beta$). The tissue or organ may be brain tissue, and the non-human mammal may be a rat or other rodent.

There is also disclosed an in vivo assay for selecting a candidate therapeutic for inhibiting congophilic and fibrillar amyloid deposition/persistence, comprising a) administering a candidate reagent to a first animal in a first infusate comprising an amyloid protein and clean perlecan or the ~220 kDa HSPG by continuous infusion at an infusion site into said tissue or organ, b) selecting the candidate reagent as a candidate therapeutic for inhibiting congophilic and fibrillar amyloid deposition/persistence if the first infusate diminishes Congo red and Thioflavin S staining indicative of fibrillar amyloid deposition/persistence at the infusion site, as compared with a second animal receiving a second infusate consisting essentially of the amyloid protein and perlecan or the ~220 kDa HSPG.

A method of perlecan isolation (from the EHS tumor) which produces "clean" (i.e. substantially "pure") perlecan is disclosed. Clean perlecan is thus produced in sufficient quantities for use in a number of different in vitro and in vivo assays. In addition, this isolation method exploits a newly discovered aggregating property of a ~220 kDa heparan sulfate proteoglycan (HSPG) observed during gel filtration chromatography, which allows it to be effectively separated from non-aggregating perlecan. The method employs specific cation exchange, anion exchange, molecular sieve chromatography and immobilized GAG affinity chromatography. It is demonstrated that there are no other contaminating proteins in the perlecan and HSPG preparations, and that the perlecan core protein is intact. Improved, clean perlecan based, rodent models of fibrillar amyloid protein deposition, accumulation and/or persistence in tissues are disclosed.

These and other features and advantages of the present invention will become more fully apparent when the following detailed description of the invention is read in conjunction with the accompanying figures.

BRIEF DESCRIPTION OF THE DRAWINGS

The following drawings are illustrative of embodiments of the invention and are not meant to limit the scope of the invention.

FIG. 6 is a black and white photograph of Western blot analysis to demonstrate the absence of laminin, fibronectin or type IV collagen in the final perlecan preparations.

FIG. 8 is a color photomicrograph demonstrating the infusion of the perlecan product plus beta-amyloid protein (Aβ) into rodent hippocampus for the establishment of a reliable animal model of Aβ amyloid deposition/persistence.

BEST MODE OF CARRYING OUT THE INVENTION

Figure 1:
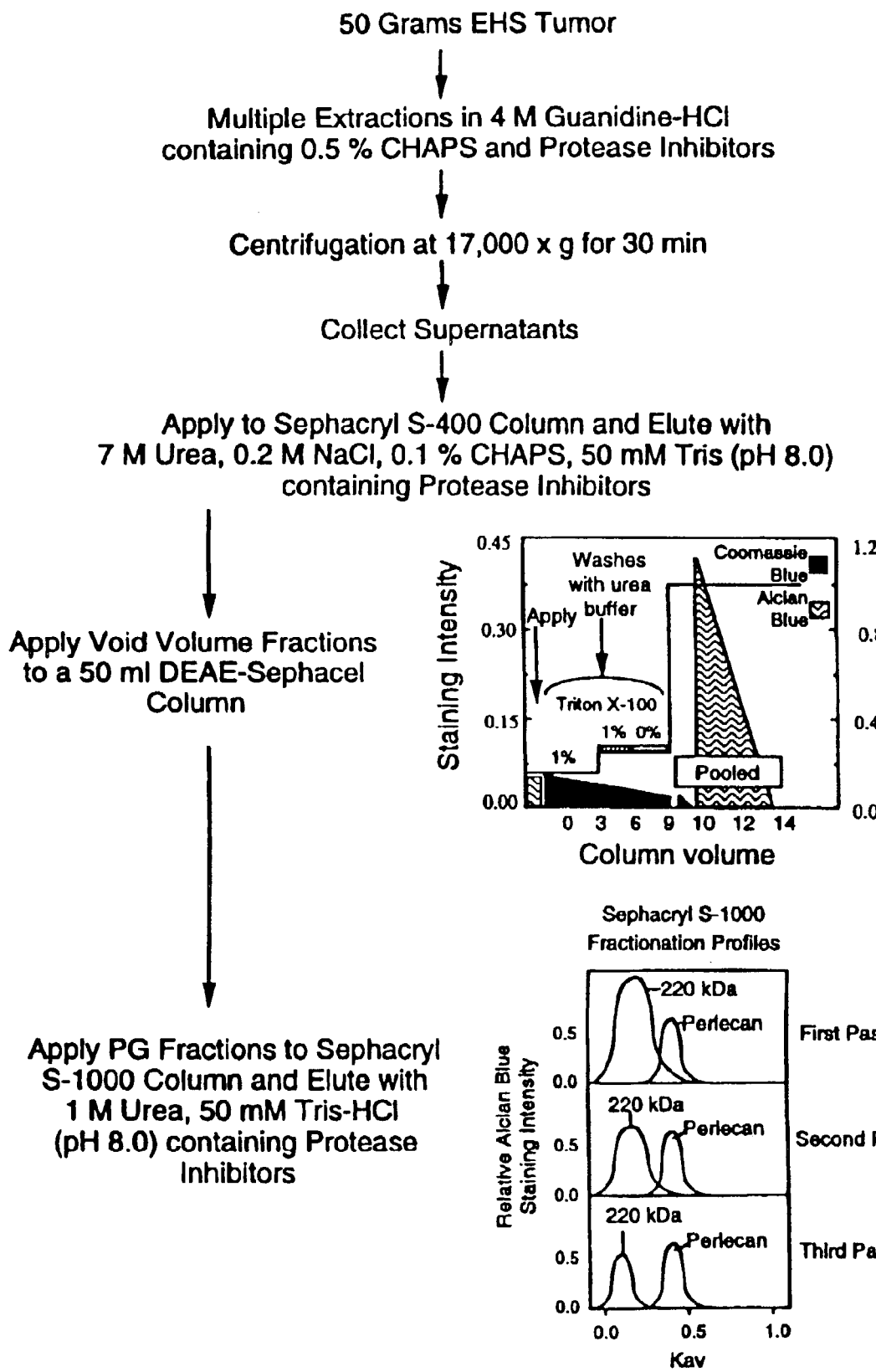
FIG. 1 is a schematic describing a protocol for clean perlecan purification (isolation) from the Engelbreth-Holm-Swarm tumor.

The following sections are provided by way of additional background to better appreciate the invention.

Structure of Perlecan

The DNA sequence for human perlecan encodes a protein core with a molecular weight of approximately 467 kDa (Murdoch, A. D. et al, *J. Biol. Chem.* 267:8544–8557, 1992) whereas the DNA sequence for mouse perlecan encodes a protein core with a molecular weight of approximately 396 kDa (Noonan, D. M. et al, *J. Biol. Chem.* 266:22939–22947, 1991). The genes for human (Murdoch, A. D. et al, *J. Biol. Chem.* 267:8544–8557, 1992; Kallunki, P. and Tryggvason, K. *J. Cell Biol.* 116:559–571, 1992) and mouse (Noonan, D. M. et al, *J. Biol. Chem.* 266:22939–22947, 1991) perlecan have been cloned and the predicted core protein consists of five distinct domains. Domain I contains the proposed heparan sulfate GAG attachment sites and is unique to perlecan showing no similarity to other known protein sequences. The location of the three Ser-Gly consensus heparan sulfate GAG attachment sites at the N-terminus corresponds with the number and position of known GAG chains (Kokenyesi, R. and Silbert, J. E. *Biochem. Biophys. Res. Comm.* 211: 262–267, 1995). Domain II is homologous to the LDL binding domain present in the LDL-receptor, whereas Domain III has homology to the globule-rod regions of the laminin short arms. Domain IV is a highly repetitive region with numerous immunoglobulin-like repeats that show the highest similarity to neural cell adhesion molecule (N-CAM). Domain V has three globular repeats very similar to the domain G repeats in the laminin A chain and the equivalent segment of the A chain homologue, merosin, and two epidermal growth factor-like regions (Noonan, D. M., and Hassell, J. R., *Kidney Int.* 43:53–60, 1993). The perlecan core protein is therefore a unique and large macromolecule with homology to a number of other well known proteins.

Perlecan Production by Different Cell Types and its Postulated Roles in the Pathogenesis of Amyloidoses Perlecan is present on all basement membranes (Dziadek et al, *EMBO J.* 4, 905–912, 1985; Kato et al, *J. Cell Biol.* 106:2203–2210, 1988; Murdoch et al, *J. Histochem. Cytochem.* 42: 239–249, 1994) and was previously cloned from both human (Murdoch et al, *J. Biol. Chem.* 267: 8544–8557, 1992; Kallunki and Tryggvason, *J. Cell. Biol.* 116:559–571, 1992) and mouse (Noonan et al, *J. Biol. Chem.* 266:22939–22947, 1991). Perlecan is known to be produced by different cell types including endothelial cells (Kinsella and Wight, *Biochem.* 27:2136–2144, 1988; Saku and Furthmayr, *J. Biol. Chem.* 264:3514–3523, 1989; Rescan et al, *Am. J. Path.* 142:199–208, 1993), smooth muscle cells (Nikkari et al, *Am. J. Path.* 144: 1348–1356, 1994), fibroblasts (Murdoch et al, *J. Histochem. Cytochem.* 42:239–249, 1994; Heremans et al, *J. Cell Biol.* 109:3199–3211, 1989), epithehal cells (Morris et al, *In Vitro Cell Dev. Biol.* 30:120–128, 1994; Ohji et al, *Invest. Opth. Vis. Sci.* 35:479–485, 1994; Van Det et al, *Biochem. J.* 307:759–768, 1995), and synovial cells (Dodge et al, *Lab. Invest.* 73:649–657, 1995). Perlecan is also synthesized by bone marrow derived cells (Grässel et al, *Mol. Cell Biochem.* 145:61–68, 1995) and is present in cancerous tissue including metastatic melanomas (Cohen et al, *Cancer Res.* 54:5771–5774, 1994), human breast tumors (Guelstein et al, *Int. J. Cancer* 53:269–277, 1993), and liver tumors (Kovalsky et al, *Acta Biomed. Ateneo Parmense* 64:157–163, 1993). Both F9 embryonal carcinoma cells (which form parietal endoderm) and P19 embryonal carcinoma cells (which form cholinergic neurons) also demonstrate marked increased perlecan expression and synthesis upon differentiation (Chakravarti et al, *Dev. Dyn.* 197:107–114, 1993; Sekiguchi et al, *J. Neurosc. Res.* 38:670–686, 1994).

Perlecan is postulated to play a primary role in the pathogenesis of Alzheimer's disease (AD) amyloidosis, as well as in other types of central nervous system and systemic amyloidoses (reviewed in Snow, and Wight, *Neurobiol. Aging* 10:481–497, 1989). Only heparan sulfate proteoglycans have been found to be immunolocalized to all three major lesions (i.e. neuritic plaques, neurofibrillary tangles and cerebrovascular amyloid deposits) in Alzheimer's disease brain and specifically to the beta-amyloid protein (A$\beta$)-containing amyloid fibrils in both amyloid plaques and congophilic angiopathy (Snow et al, *Am. J. Path.* 133: 456–463, 1988; Snow and Wight, *Neurobiol. Aging* 10:481–497, 1989; Perlmutter and Chui, *Brain Res. Bull.* 24:677–686, 1990; Snow et al, *Am. J. Path.* 137:1253–1270, 1990; Su et al, *Neuroscience* 51:801–813,1992; Van Gool et al, *Dementia* 4:308–314, 1993). Accumulating evidence suggests that perlecan is a major heparan sulfate proteoglycan present within the A$\beta$-containing amyloid deposits in Alzheimer's disease (Snow et al, *Am. J. Path.* 133:456–463, 1988; Snow and Wight, *Neurobiol. Aging,* 10:48–497, 1989; Snow et al, *Am. J. Path.* 137:1253–1270, 1990; Snow et al, *Am. J. Path.* 144:337–347, 1994) and may play a primary role in A$\beta$ fibril formation, deposition, accumulation and persistence. The consistent co-localization of perlecan to A$\beta$ deposits which exist in both a fibrillar and non-fibrillar form (Snow et al, *Am. J. Path.* 144:337–347, 1994) is probably due to perlecan's high affinity interactions with A$\beta$ (Snow et al, *J. Neuropath. Exp. Neurol.* 48:352, 1989 Abstract; Buee et al, *Brain Res.* 601:154–163, 1993; Buee et al, *Brain Res.* 627:199–204, 1993; Snow et al, *Arch. Biochem. Biophys.* 320:84–95, 1995) and with beta-amyloid precursor proteins (Narindrasorasak et al, *J. Biol. Chem.* 266:12878–12883, 1991). Residues 13–16 of A$\beta$ have been identified as a perlecan binding site (Snow et al, *J. Neuropath. Exp. Neurol.* 48:352, 1989 Abstract; Brunden et al, J. Neurochem. 61:2147–2154, 1993; Snow et al, Arch. Biochem. Biophys. 320:84–95, 1995). This region contains a heparin/heparan sulfate binding consensus sequence (Cardin and Weintraub, *Arterioscl.* 9:21–32, 1989), and is adjacent to the postulated alpha-secretase cleavage site on A$\beta$ (at Lys-16). Once bound, perlecan is believed to influence the secondary structure and/or aggregation properties of A$\beta$ and/or beta-amyloid precursor proteins (Fraser et al, *J. Neurochem.* 59:1531–1540, 1992). Perlecan also appears to play a role in stabilizing fibrillar A$\beta$ amyloid when deposited in vivo (Snow et al, *Neuron* 12:219–234, 1994; Snow et al, *Soc. Neurosc. Abst.* 21:1292, 1995 Abstract), and protects A$\beta$ from degradation by proteases as recently demonstrated in vitro (Gupta-Bansal et al, *J. Biol. Chem.* 270:18666–18671, 1995). The combined results described above suggest that perlecan is an important macromolecule that has now been implicated at several key steps in the pathogenesis of A$\beta$ amyloidosis in AD.

Other Amyloid Diseases

The "amyloid diseases" consist of a group of clinically and generally unrelated human diseases which all demonstrate a marked accumulation in tissues of an insoluble extracellular substance known as "amyloid", and usually in an amount sufficient to impair normal organ function. Rokitansky in 1842 (Rokitansky, "*Handbuch der pathologischen Anatomie*", Vol. 3, Braumuller and Seidel, Vienna) was the first to observe waxy and amorphous looking tissue deposits in a number of tissues from different patients. However, it wasn't until 1854 when Virchow (Virchow, *Arch. Path. Anat.* 8:416, 1854) termed these deposits as "amyloid" meaning "starch-like" since they gave a positive staining with the sulfuric acid-iodine reaction, which was used in the 1850's for demonstrating cellulose. Although cellulose is not a constituent of amyloid, nonetheless, the staining that Virchow observed was probably due to the present of proteoglycans (PGs) which appear to be associated with all types of amyloid deposits. The name amyloid has remained despite the fact that Friederich and Kekule in 1859 discovered the protein nature of amyloid (Friedrich and Kekule, *Arch. Path. Anat. Physiol.* 16:50, 1859). For many years, based on the fact that all amyloids have the same staining and structural properties, lead to the postulate that a single pathogenetic mechanism was involved in amyloid deposition, and that amyloid deposits were thought to be composed of a single set of constituents. Current research has clearly shown that amyloid is not a uniform deposit and that amyloids may consist of different proteins which are totally unrelated (Glenner, *N. England J. Med.* 302:1283–1292, 1980).

Although the nature of the amyloid itself has been found to consist of completely different and unrelated proteins, all amyloids appear similar when viewed under the microscope due to amyloid's underlying protein able to adapt into a fibrillar structure. All amyloids regardless of the nature of the underlying protein 1) stain characteristically with the Congo red dye and display a classic red/green birefringence when viewed under polarized light (Puchtler et al, *J. Histochem. Cytochem.* 10:355–364, 1962), 2) ultrastructurally consists of fibrils with a diameter of 7–10 nanometers and of indefinite length, 3) adopt a predominant beta-pleated sheet secondary structure. Thus, amyloid fibrils viewed under an electron microscope (30,000 times magnification) from the post-mortem brain of an Alzheimer's disease patient would look nearly identical to the appearance of amyloid present in a biopsied kidney from a rheumatoid arthritic patient. Both these amyloids would demonstrate a similar fibril diameter of 7–10 nanometers.

In the mid to late 1970's amyloid was clinically classified into 4 groups, primary amyloid, secondary amyloid, familial amyloid and isolated amyloid. Primary amyloid, is amyloid appearing de novo, without any preceding disorder. In 25–40% of these cases, primary amyloid was the antecedent of plasma cell dysfunction such as the development of multiple myeloma or other B-cell type malignancies. Here the amyloid appears before rather than after the overt malignancy. Secondary amyloid, appeared as a complication of a previously existing disorder. 10–15% of patients with multiple myeloma eventually develop amyloid (Hanada et al, *J. Histochem. Cytochem.* 19:1–15, 1971). Patients with rheumatoid arthritis, osteoarthritis, ankylosing spondylitis can develop secondary amyloidosis as with patients with tuberculosis, lung abscesses and osteomyelitis (Benson and Cohen, *Arth. Rheum.* 22:36–42, 1979; Kamei et al, *Acta Path. Jpn.* 32:123–133, 1982; McAdam et al, *Lancet* 2:572–575, 1975). Intravenous drug users who self-administer and who then develop chronic skin abscesses can also develop secondary amyloid (Novick, *Mt. Sin. J. Med.* 46:163–167, 1979). Secondary amyloid is also seen in patients with specific malignancies such as Hodgkin's disease and renal cell carcinoma (Husby et al, *Cancer Res.* 42:1600–1603, 1982). Although these were all initially classified as secondary amyloid, once the amyloid proteins were isolated and sequenced many of these turned out to contain different amyloid proteins.

The familial forms of amyloid also showed no uniformity in terms of the peptide responsible for the amyloid fibril deposited. Several geographic populations have now been identified with genetically inherited forms of amyloid. One group is found in Israel and this disorder is called Familial Mediterranean Fever and is characterized by amyloid deposition, along with recurrent inflammation and high fever (Mataxas, *Kidney* 20:676–685, 1981). Another form of inherited amyloid is Familial Amyloidotic Polyneuropathy, and has been found in Swedish (Skinner and Cohen, *Biochem. Biophys. Res. Comm.* 99:1326–1332, 1981), Portuguese (Saraiva et al, *J. Lab. Clin. Med.* 102:590–603, 1983; *J. Clin. Invest.* 74:104–119, 1984) and Japanese (Tawara et al, *J. Lab. Clin. Med.* 98:811–822, 1981) nationalities. Amyloid deposition in this disease occurs predominantly in the peripheral and autonomic nerves. Hereditary amyloid angiopathy of Icelandic origin is an autosomal dominant form of amyloid deposition primarily affecting the vessels in the brain, and has been identified in a group of families found in Western Iceland (Jennson et al, *Clin. Genet.* 36:368–377, 1989). These patients clinically have massive cerebral hemorrhages in early life which usually causes death before the age of 40.

The primary, secondary and familial forms of amyloid described above tend to involve many organs of the body including heart, kidney, liver, spleen, gastrointestinal tract, skin, pancreas, and adrenal glands. These amyloid diseases are also referred to as "systemic amyloids" since so many organs within the body demonstrate amyloid accumulation. For most of these amyloidoses, there is no apparent cure or effective treatment and the consequences of amyloid deposition can be detrimental to the patient. For example, amyloid deposition in kidney may lead to renal failure, whereas amyloid deposition in heart may lead to heart failure. For these patients, amyloid accumulation in systemic organs leads to eventual death generally within 3 to 5 years.

Isolated forms of amyloid, on the other hand, tend to involve a single organ system. Isolated amyloid deposits have been found in the lung, and heart (Wright et al, *Lab. Invest.* 30:767–773, 1974; Pitkanen et al, *Am. J. Path.* 117:391–399, 1984). Up to 90% of type II diabetic patients (non-insulin dependent form of diabetes) have isolated amyloid deposits in the pancreas restricted to the beta cells in the islets of Langerhans (Johnson et al, *New Engl. J. Med.* 321:513–518, 1989; *Lab. Invest.* 66:522–535, 1992). Isolated forms of amyloid have also been found in endocrine tumors which secrete polypeptide hormones such as in medullary carcinoma of the thyroid (Butler and Khan, *Arch. Path. Lab. Med.* 110:647–649, 1986; Berger et al, *Virch. Arch. A Path. Anat. Hist.* 412:543–551, 1988). A serious complication of long term hemodialysis is amyloid deposited in the medial nerve and clinically associated with carpal tunnel syndrome (Gejyo et al, *Biochem. Biophys. Res. Comm.* 129:701–706, 1985; *Kidney Int.* 30:385–390, 1986). By far, the most common type and clinically relevant type of organ-specific amyloid, and amyloid in general, is that found in the brains of patients with Alzheimer's disease (see U.S. Pat. No. 4,666,829 and Glenner and Wong, *Biochem. Biophys. Res. Comm.* 120:885–890, 1984; Masters et al, *Proc. Natl. Acad. Sci., USA* 82:4245–4249, 1985). In this disorder, amyloid is predominantly restricted to the central nervous system. Similar deposition of amyloid in the brain occurs in Down's syndrome patients once they reach the age of 35 years (Rumble et al, *New England J. Med.* 320:1446–1452, 1989; Mann et al, *Neurobiol. Aging* 10:397–399, 1989).

Other types of central nervous system amyloid deposition include rare but highly infectious disorders known as the prion diseases which include Creutzfeldt-Jakob disease, Gerstmann-Straussler syndrome, and kuru (Gajdusek et al, *Science* 197:943–960, 1977; Prusiner et al, *Cell* 38:127–134, 1984; Prusiner, *Scientific American* 251:50–59, 1984; Prusiner et al, *Micr. Sc.* 2:33–39, 1985; Tateishi et al, *Ann. Neurol.* 24:35–40, 1988).

It was misleading to group the various amyloidotic disorders strictly on the basis of their clinical features, since when the major proteins involved were isolated and sequenced, they turned out to be different. For example, amyloid seen in rheumatoid arthritis and osteoarthritis, now known as AA amyloid, was the same amyloid protein identified in patients with the familial form of amyloid known as Familial Mediterranean Fever. Not to confuse the issue, it was decided that the best classification of amyloid should be according to the major protein found, once it was isolated, sequenced and identified.

Thus, amyloid today is classified according to the specific amyloid protein deposited. The amyloid diseases include, but are not limited to, the amyloid associated with Alzheimer's disease, Down's syndrome and hereditary cerebral hemorrhage with amyloidosis of the Dutch type (wherein the specific amyloid is now known as the beta-amyloid protein or A$\beta$), the amyloid associated with chronic inflammation, various forms of malignancy and Familial Mediterranean Fever (AA amyloid or inflammation-associated amyloidosis), the amyloid associated with multiple myeloma and other B-cell abnormalities (AL amyloid), the amyloid associated with type II diabetes (amylin or islet amyloid), the amyloid associated with the prion diseases including Creutzfeldt-Jakob disease, Gerstmann-Straussler syndrome, kuru and animal scrapie (PrP amyloid), the amyloid associated with long-term hemodialysis and carpal tunnel syndrome (beta$_2$-microglobulin amyloid), the amyloid associated with senile cardiac amyloid and Familial Amyloidotic Polyneuropathy (prealbumin or transthyretin amyloid), and the amyloid associated with endocrine tumors such as medullary carcinoma of the thyroid (variants of procalcitonin).

Perlecan Isolation from the Engelbreth-Holm-Swarm Tumor

The most commonly used source for isolation of perlecan is the EHS tumor which is routinely grown in the hind legs of mice (Hassell et al., *J. Biol. Chem.* 260:8098–8105, 1985; Kato et al., *J. Biol. Chem.* 262:7180–7188, 1987; Ledbetter et al., *Biochem.* 26:988–995, 1987; Paulsson et al., *J. Mol. Biol.* 197:297–313, 1987). Known methods of perlecan isolation from the EHS tumor employ a series of extractions and cesium chloride centrifugation (Fujiwara et al., *Eur. J. Biochem.* 143:145–157, 1984; Hassell et al., *J. Biol. Chem.* 260:8098–8105, 1985; Kato et al., *J. Biol. Chem.* 262: 7180–7188, 1987; Ledbetter et al., *Biochem.* 26:988–995, 1987; Paulsson et al., *J. Mol. Biol.* 197:297–313, 1987). Cesium chloride density gradient centrifugation is employed to separate the two major PGs produced by the EHS tumor, namely perlecan (referred to in the literature as the "low density HSPG"), and a smaller HSPG of $M_r$ 200–400 kDa which has not been fully characterized (referred to as the "high density HSPG") (Fujiwara et al., *Eur. J. Biochem.* 143:145–157, 1984; Hassell et al., *J. Biol. Chem.* 260: 8098–8105, 1985; Kato et al., *J. Biol. Chem.* 262:7180–7188, 1987; Ledbetter et al., *Biochem.* 26:988–995, 1987; Paulsson et al., *J. Mol. Biol.* 197:297–313, 1987). Some of the shortcomings of using these known methods of perlecan isolation include: a) contamination by other proteins and/or basement membrane components (i.e. Laminin, fibronectin and type IV collagen) produced by the EHS tumor, b) contamination due to the presence of free GAG chains, and c) degradation of the perlecan core protein.

In the present invention, methods of perlecan purification in quantities appropriate for various assay and therapeutic needs are described. These methods exploit a newly discovered aggregating property of the ~220 kDa PG observed during gel filtration chromatography, which property was not exhibited by perlecan. In addition, the purification protocol of the invention employs a higher pH (preferably pH=8.0), in a higher pH range (pH=7.4 to 8.0+), than conventionally specified (Hassell et al., *J. Biol. Chem.* 260:8098–8105, 1985; Kato et al., *J. Biol. Chem.* 262:7180–7188, 1987; Ledbetter et al., *Biochem.* 26:988–995, 1987), and which higher pH is believed to significantly attenuate or block protein-GAG interactions (such as those described by Heinedgard and Sommarin, *Methods Enzym.* 144:319–372, 1987), thereby advantageously decreasing the involvement of possible contaminants which might otherwise bind to perlecan during fractionation. The perlecan preparations obtained from this novel methodology are of consistently high quality as demonstrated by a demonstrably intact core protein, and by absence of any significant quantity of contaminating proteins and/or free GAG chains.

Infusion of this perlecan product into rodent brain, in the presence of Aβ, consistently leads to fibrillar Aβ amyloid deposits in the brain tissue in 100% of tested animals, but which is only observed in 60% of animals following infusion of Aβ alone.

EXAMPLES

The following examples are set forth to provide those with ordinary skill in the art with the disclosure and description of detailed methodology to obtain "clean" perlecan, and for the isolation of a ~220 kDa heparan sulfate proteoglycan (HSPG) from EHS tumor. However, it should not be construed that the invention is limited to these specific examples.

Materials Used for the Examples Describing the Invention

C57BL mice were purchased from B & K Universal (Kent, Wash.). Nembutal was from Abbott Laboratories (North Chicago, Ill.). Alcian blue, Coomassie blue, EHS laminin, bovine plasma fibronectin, EHS type IV collagen, affinity purified rabbit polyclonal anti-laminin (L9393), heparinases I, II and III, BSA, normal goat serum, guanidine-HCl, CHAPS, Tris-HCl, N-ethylmaleimide (NEM), 6-aminohexanoic acid, benzamidine-HCl, phenylmethylsulfonyl fluoride (PMSF), silver nitrate, sodium bicarbonate, sodium nitrite and sodium citrate were all purchased from the Sigma Chemical Company (St. Louis, Mo.). Methanol, potassium acetate, glutaraldehyde, sodium hydroxide, ammonium hydroxide, sodium azide, formaldehyde, acetic acid, sodium chloride, (ethylenediamine)tetraacetic acid (EDTA), and urea were all from J. T. Baker Inc. (Phillipsburg, N.J.). Absolute ethanol was from McCormick (Pekin, Ill.). Sephacryl S-400 and S-1000, DEAE-Sephacel and all columns used for analysis were purchased from Pharmacia (Uppsala, Sweden). Triton X-100 was from Boehringer Mannheim (Indianapolis, Minn.). The conductivity meter with Model number 2052 was from VWR Scientific (Seattle, Wash.). The mini-protean II electrophoresis system, mini transblot electrophoresis transfer cell, pre-cast polyacrylamide gradient gels (4–15%), electrophoresis running buffer, SDS sample buffer, and pre-stained molecular weight protein standards were from Bio-Rad (Richmond, Calif.). Nitrocellulose (0.45_m) was from Schleicher and Schuell (Keene, N.H.). Anti-laminin polyclonal antibody (AB756), and anti-fibronectin polyclonal antibody (AB1941) were Chemicon (Temicula, Calif.). Biotinylated secondary antibodies (goat anti-rat and goal anti-rabbit) were purchased from Jackson ImmunoResearch (West Grove, Pa.). Avidin alkaline phosphatase conjugate and alkaline phosphatase substrate solution (Vectastain ABC kit) were from Vector Labs, Inc. (Burlingame, Calif.). Tween-20 was from Calbiochem Corp. (La Jolla, Calif.). Anti-perlecan core protein monoclonal antibody (HK-102) was a generous gift from Dr. Koji Kimata (Aichi, Japan).

Example 1

Perlecan Purification from the Engelbreth-Holm-Swarm Tumor

FIG. 1 shows a protocol for perlecan purification from the EHS tumor. The EHS tumor was maintained in the right or left hind leg muscle of C57Bl mice following injection of tumor cells as previously described (Swarm, *J. Natl. Cancer Inst.* 31:953–975, 1963; Swarm et al., *J. Natl. Cancer Inst.* 33:657–672, 1964; Orkin et al., *J. Exp. Med.* 145:204–220, 1977). The tumors were usually maintained in the mice hind legs for 3–4 weeks usually attaining a growth of approximately 3–4 grams. In accordance with National Institute of Health (Bethesda, Md., USA) Animal Care and Use Guidelines, the animals were sacrificed by lethal injection of Nembutal (0.50 ml of 50 mg/ml solution per mouse), before the tumor tissue reached an approximate weight of 4 grams. EHS tumor tissue was harvested from the mice as previously described (Orkin et al., *J. Exp. Med.* 145:204–220, 1977). All extraction steps (described below) were carried out by agitation using a rotary shaker at 600 rpm (Model M65825, Barnstead/Thermolyne, Dubuque, Iowa). The tumor tissue (50 grams at a time) was routinely minced and extracted with 2.5 tissue volumes of 50 mM Tris-HCl (pH 7.5), 3.4 M NaCl, containing a protease inhibitor cocktail including 10 mM EDTA, 10 mM NEM, 10 mM 6-aminohexanoic acid, 5.0 mM benzamidine-HCl, and 1 mM PMSF.

The supernatants were collected following centrifugation at 17,000×g for 30 minutes. This high salt extraction was repeated and the resulting pellet obtained was extracted with 2.5 tissue volumes of 4M guanidine-HCl, 0.5% (w/v) CHAPS, 50 mM Tris-HCl (pH 7.5) containing a protease inhibitor cocktail (as described above) for 3 hours at 4° C. The supernatants were again collected following centrifugation at 17,000×g for 30 minutes. Additional extractions of the remaining pellet were achieved using 1.5 tissue volumes with guanidine-HCl (as described above), first for 2 hours, and then overnight. The guanidine extracts were then pooled and applied (80 mls at a time) to Sephacryl S-400 columns (4.8×28 cm). Samples were then eluted using a urea buffer containing 7M urea, 0.2M NaCl, 0.1% (w/v) CHAPS, 50 mM Tris-HCl (pH 8.0) containing protease inhibitors as described above. The void volume fractions (believed to contain perlecan) from the Sephacryl S-400 column were then pooled and supplemented with 0.5% Triton X-100 (v/v) and applied to a 50 ml DEAE-Sephacel column packed in a 60 ml plastic syringe equilibrated with urea buffer. Contaminant proteins and non-PGs were removed by first washing the column with 3 column volumes of urea buffer containing 1% Triton X-100, followed by 3 column volumes of urea buffer containing 0.25M NaCl and 1% Triton X-100, and then 3 column volumes of urea buffer containing 0.25 M NaCl without Triton X-100. Bound PGs were then eluted with 5 column volumes of urea buffer containing 1M NaCl or 3M NaCl. The 3M NaCl elutions were used to determine whether tightly bound PGs not eluted with 1M NaCl still remained bound to the column.

PGs obtained from the DEAE-Sephacel column were first loaded onto a Sephacryl S-500 column (2.6×60 cm) in order to try to separate the 220 kDa PG from perlecan (700–800 kDa). In a preliminary study, we found the Sephacryl S-500 column was not able to properly separate the 220 kDa PG from perlecan (both were found in the void volume fractions), due to the self-aggregating ability of the 220 kDa PG. Even the use of dissociating buffers including, a) 4M guanidine-HCl, 0.5% CHAPS, and 50 mM Tris-HCl (pH 7.5), b) 7M urea, 0.2M NaCl, 1% SDS (w/v), and 50 mM Tris-HCl (pH 8.0) and c) 7M urea, 0.2M NaCl, 0.1% CHAPS, and 50 mM Tris-HCl (pH 8.0), were not able to prevent the aggregation of the 220 kDa PG. Separation of the 220 kDa PG from perlecan was finally achieved using a Sephacryl S-1000 column (5×95 cm) under associating conditions (1M urea buffer containing 50 mM Tris-HCl and protease inhibitors including 1.4 mM EDTA, 1.4 mM NEM, 1.4 mM 6-aminohexanoic acid, 0.7 mM benzamidine, and 0.14 mM PMSF; pH 8.0).

PGs eluted from DEAE-Sephacel were loaded (50 mls per run) onto the Sephacryl S-1000 column (as described above). PGs eluted from the Sephacryl S-1000 column were monitored by SDSPAGE analysis in order to assess the purity of perlecan and other HSPGs produced. For this analysis, 100 µl aliquots of each 60 ml fraction was precipitated with 4 volumes of absolute ethanol by cooling on dry ice for 1 hour, and then centrifuged on a microcentrifuge at 12,000×g for 20 minutes, and run on SDS-PAGE as described below. Pooled fractions (from 5 separate runs) containing perlecan ($K_{av}$=0.29–0.54) were then concentrated on and eluted from a 15 ml DEAE-Sephacel column with 3M NaCl, and rechromatographed onto the Sephacryl S-1000 (as described above). Usually three passes through the Sephacryl S-1000 column gave high quality perlecan preparations free from any other contaminating HSPGs (i.e. 220 kDa PG) or other PGs. The perlecan fractions were pooled and concentrated onto a 10 ml DEAE-Sephacel column and ethanol precipitated (as described above). The resulting pellets were dissolved in 3–5 ml of double distilled water and extensively dialyzed against double distilled water until the conductivity of the end product contained very little to no salt (2–3 µmhos) as measured using a digital conductivity meter. The final perlecan product was then freeze-dried and stored. The final purity of the perlecan preparations were further assessed by Alcian blue staining, Coomassie Blue staining, silver staining, and a series of Western blots (as described below).

SDS-PAGE

SDS-PAGE was performed according to the method of Laemmli Laemmli, Nature 227:680–685, 1970) using a Mini-Protean II electrophoresis system with precast 4–15% polyacrylamide gels. In order to examine perlecan quality on SDS-PAGE following the Sephacryl S-1000 chromatography described above, pelleted fractions were redissolved in 20 µl of 1× reducing SDS sample buffer, heated for 5 minutes in a boiling water bath, and electrophoresed at 200V for 45 minutes along with pre-stained molecular weight protein standards. All gel staining and washing steps were carried out with mild agitation using a rotary shaker.

Alcian Blue, Coomassie Blue and Silver Staining

Alcian blue staining of SDS-PAGE gels was employed to detect PGs (Wall and Gyi, Anal Biochem. 175:298–299, 1988) using a modified method (Castillo and Snow, unpublished observations). Following electrophoresis, gels were rinsed 3 times (for 20 minutes each) with 50% methanol, 10% acetic acid (v/v) and then stained for 2 hours with 0.1% Alcian blue in 50% methanol and 10% acetic acid. For destaining, the gels were rinsed 6–10 times for 20 min each, with the same solution as described above, but without Alcian blue. Non-PG proteins were visualized by staining for 2 hours in the same solution (described above) containing 0.2% (w/v) Coomassie Brilliant Blue and destaining in a similar manner as in Alcian Blue staining protocol (described above).

Some gels were also stained with silver to detect any contaminating proteins in our preparations, using the methods previously described (Oakley et al., Anal. Biochem. 105:361–363, 1980), with slight modifications. Briefly, gels were washed for 25 minutes in 50% methanol and 10% acetic acid (v/v), followed by three washes (10 minutes each) in 10% ethanol and 5% acetic acid (v/v), and then two washes (10 minutes each) with distilled deionized (DD) water. Gels were then fixed for 20–40 minutes with freshly made 1% (v/v) glutaraldehyde and 0.2 M sodium bicarbonate, and washed twice (10 minutes each) with DD water. The gels were then stained for 30 minutes with freshly made 0.8% $AgNO_3$ (w/v), 0.07% NaOH (w/v), 1.3% $NH_4OH$ (v/v) and 15% ethanol (v/v), rinsed three times (10 minutes each) with DD water, and developed using a solution containing 0.005% sodium citrate (w/v), 0.037% formaldehyde (v/v), and 10% ethanol (v/v). The silver reaction was stopped by adding 5% acetic acid (v/v).

Digestion with Heparitinase/Heparinase and Nitrous Acid

Prior to SDS-PAGE, some of the ethanol precipitated HSPGs were digested by incubation overnight at 41° C. with 1.0 Unit each of heparinases I, II and III (heparitinase) in 90 µl of digestion buffer consisting of 100 mM Tris-HCl, 2.5 mM calcium acetate, 5.0 mM 6-aminohexanoic acid, 2.5 mM benzamidine-HCl, 5.0 mM NEM, and 0.50 mM PMSF (pH 7.0). The next day, digested samples were precipitated by adding 3.5 volumes of 95% ethanol, 1.5% potassium acetate (w/v), cooled on dry ice for 1 hour and then centrifuged at 12,000×g for 20 minutes. For Western blotting of perlecan core protein, the pellets were redissolved in 20 µl of non-reducing SDS sample buffer (since reduction eliminates the antigenic sites recognized by anti-HK-102) (Kato et al., J. Cell Biol. 106:2203–2210, 1988).

In addition, prior to SDS-PAGE, some of the ethanol precipitated HSPG samples were digested with nitrous acid (1 µl/1 µg HSPG) using $NaNO_2$ in 1.8M acetic acid at a final concentration of 0.24 M (44). Following a 20 minute nitrous acid digestion at room temperature, 5 volumes of absolute ethanol was added to the reaction mixtures, vortexed and centrifuged at 14,000×g for 20 minutes. The pellets were then dissolved in 1×SDS-PAGE sample buffer for electrophoretic separation and detection of the liberated perlecan core protein. Silver staining of heparitinase/heparinase and nitrous acid digested samples was then employed as described above.

Analysis of Final Perlecan Preparations by Western Blotting

SDS-PAGE was performed as described above and the separated proteins were transferred to nitrocellulose using a Mini transblot electrophoresis transfer cell. Electrotransfer was performed at 100V for 2 hours. Following transfer, membranes were rinsed with water and blocked overnight with 0.15% (w/v) bovine serum albumin, 1% (v/v) normal goat serum, 100 mM Tris-HCl, and 3 mM $NaN_3$ (pH 7.4). Nitrocellulose membranes probed with fibronectin antibody were blocked in the same solution described above without normal goat serum. Blots were probed with a) a monoclonal antibody (used at a 1:750 dilution) against perlecan core protein (HK-102), b) an affinity-purified polyclonal antibody (used at a 1:2000 dilution) against laminin, c) a polyclonal antibody (used at a 1:25,000 dilution) against fibronectin (AB1941) and d) a polyclonal antibody (used at a 1:25,000 dilution) against type IV collagen. The primary antibodies (described above) were diluted with Tris-buffered saline containing 100 mM Tris-HCl, 50 mM NaCl, 0.05% Tween-20, and 3 mM $NaN_3$ (pH 7.4)(TTBS). Corresponding blots were incubated with primary antibodies for three hours, washed with TTBS three times (10 minutes each), followed by a 1 hour incubation with the appropriate biotinylated secondary antibodies diluted 1:1000 with TTBS. The membranes were then rinsed three times (10 minutes each) with TTBS, probed for 30 minutes with avidin alkaline phosphatase conjugate (Vectastain), rinsed again (as described above), followed by the addition of an alkaline phosphatase substrate solution (Vectastain). Following color development, the reaction was stopped by flushing the membranes with DD water.

Example 2

Analysis at each Step of the Perlecan Isolation Procedure

Figure 2:
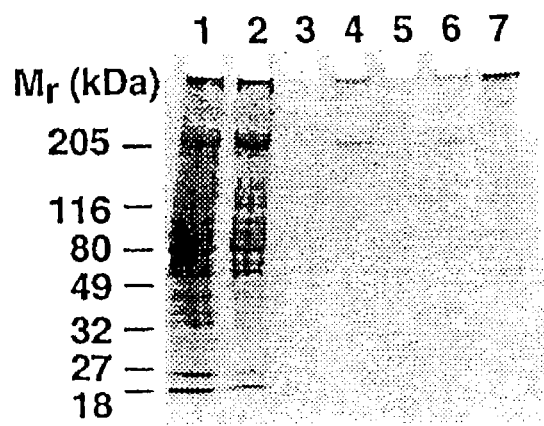
FIG. 2 is a color photograph of a SDS-PAGE gel stained with Alcian blue followed by Coomassie blue, which represents an analysis of the purity of perlecan, other proteoglycans, and/or proteins, at each step of the isolation protocol.

In order to determine the effectiveness of our perlecan isolation protocol, the presence of perlecan, other PGs and non-PG proteins were monitored at each step of the isolation method (FIG. 1). As shown in FIG. 2 lane 1, the 4M guanidine-HCl extracts contained two major PGs which were detected by Alcian blue staining (blue bands). These included a high $M_r$ PG, believed to represent perlecan (at the interface of the resolving gel), and a 220 kDa PG, believed to represent the high density HSPG, previously reported (Fujiwara et al., *Eur. J. Biochem.* 143:145–157, 1984; Hassell et al., *J. Biol. Chem.* 260:8098–8105, 1985). The guanidine-HCl extraction protocol recovered>90% of GAGs as determined using an quantitative Alcian blue staining assay (Björson, *Anal. Biochem.* 210:282–291, 1993).

In addition to the two major PGs (described above), the guanidine-HCl extracts contained many non-PG proteins as shown by Coomassie blue staining (purple stained bands in FIG. 2, lane 1). The guanidine extracts were then pooled and applied to Sephacryl S-400 columns. FIG. 2, lane 2, demonstrates the presence of the two major PGs (detected by Alcian blue) and non-PG proteins (detected by Coomassie blue) following elution from Sephacryl S-400 columns. Gel filtration chromatography using Sephacryl S-400 columns allowed for both buffer exchange and removal of many (but not all) of the non-PG proteins (compare the Coomassie blue stained bands in FIG. 2, lane 2 to FIG. 2, lane 1). The void volume fractions from the Sephacryl S-400 columns were then pooled and supplemented with 0.5% Triton X-100 (v/v) and applied to a DEAE-Sephacel column equilibrated with urea buffer.

Subsequent washing of the DEAE column with urea buffer containing Triton X-100 and 0.25M NaCl removed all of the unbound non-PG proteins, as no Coomassie-blue stained bands were apparent in the last portion of the 0.25M NaCl eluate (FIG. 2, lane 3). The subsequent 1.0 M NaCl elution from the DEAE-Sephacel column removed the two major PGs present (i.e. believed to represent perlecan and the 220 kDa PG) and demonstrated the absence of any non-PG proteins (by lack of positive Coomassie blue stained bands) (FIG. 2, lane 4). Further elution with 3M NaCl demonstrated the absence of any residual PGs or non-PG proteins bound to the DEAE column (FIG. 2, lane 5) and indicated that the majority of PGs were removed from the DEAE column using 1.0 M NaCl.

Figure 3:
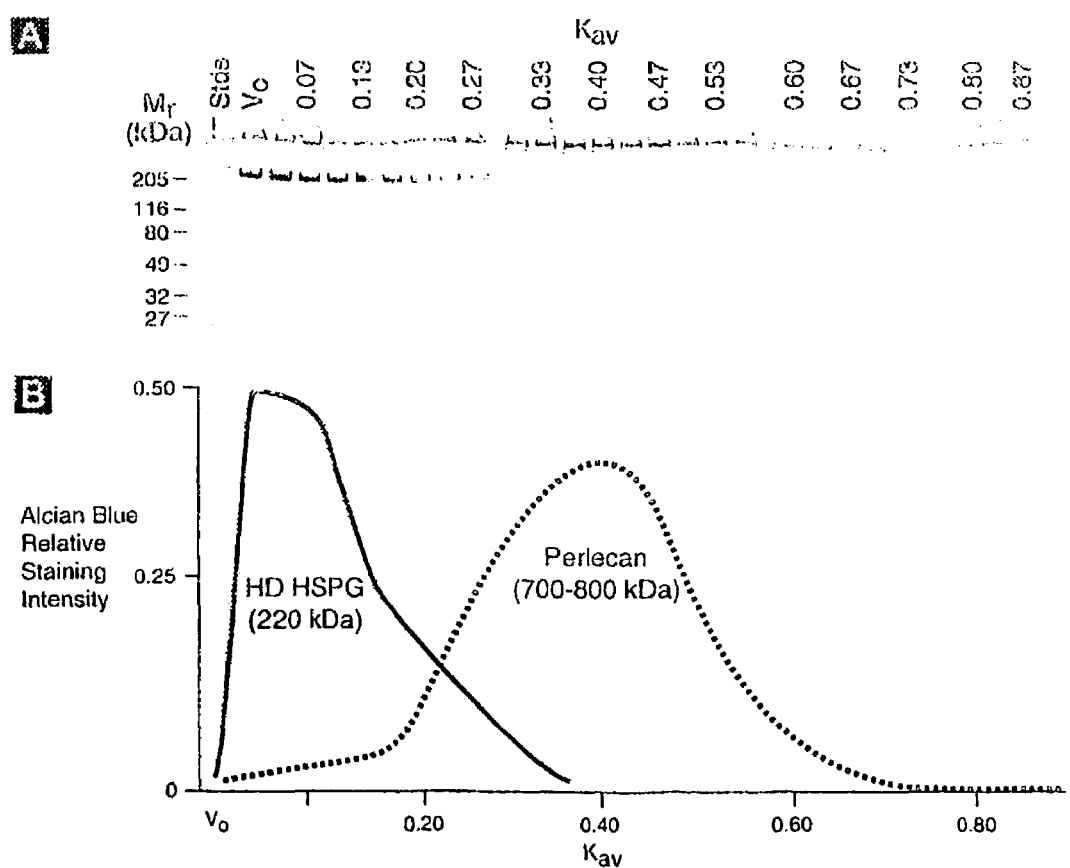
FIG. 3 is a black and white photograph of an Alcian blue stained SDS-PAGE gel of fractions obtained from a third pass through a Sephacryl S-1000 column.
Figure 4:
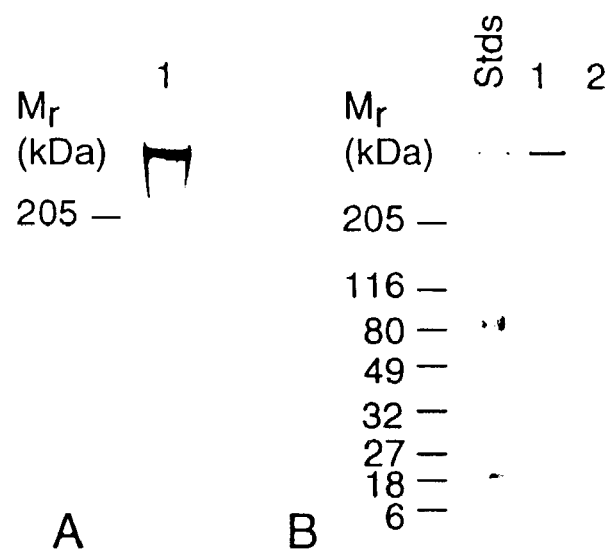
FIG. 4 is a black and white photograph of silver and Alcian blue stained SDS-PAGE gels to assess the purity of the final perlecan preparations.

In order to completely separate the 220 kDa PG component from perlecan (shown in FIG. 2, lane 4) gel filtration chromatography using a Sephacryl S-500 was evaluated. It was expected that fractionation using a Sephacryl S-500 would separate perlecan (expected to elute in the void volume) from the 220 kDa PG (expected to elute with a $K_{av}$ of ~0.45). However, under these conditions the 220 kDa PG apparently aggregated and eluted in the void volume, with perlecan eluted shortly thereafter (with a $K_{av}$=0.20). In order to achieve better separation between perlecan and the 220 kDa PG, a variety of different dissociating eluants were tried. These eluants included 4 M guanidine-HCl with 0.1% CHAPS, 7M urea with 0.1% CHAPS, and 7M urea with 1% SDS. Regardless of the eluants employed (as described above), the 220 kDa PG was always present in the void volume fractions and was present in most fractions containing perlecan. Separation of perlecan from the aggregating 220 kDa PG was achieved using a Sephacryl S-1000 column. As shown (FIG. 2, lanes 6 and 7; and FIG. 3), this column was effective in separating perlecan from the 220 kDa PG, which under these conditions still aggregated and was primarily found in the void volume fractions with a $K_{av}$<0.33 (FIG. 3). Perlecan was now effectively separated from the 220 kDa PG and was primarily present in fractions with a $K_{av}$=0.20–0.70, with a major peak at $K_{av}$=0.40; (FIG. 3). Perlecan could therefore be successfully isolated without contamination by the 220 kDa PG by pooling fractions with a $K_{av}$=0.37–0.54 (FIG. 2, lane 7 and FIG. 3). The 220 kDa PG (with only slight perlecan contamination) could also be isolated by pooling fractions with a $K_{av}$=0.0–0.37 (FIG. 2, lane 6 and FIG. 3). Any lower molecular weight GAGs observed in the pooled perlecan fractions following a second pass through the Sephacryl S-1000 column (FIG. 2, lane 7; FIG. 3A) were subsequently removed following a third pass through the Sephacryl S-1000 column, yielding a pure perlecan product (see FIGS. 4 and 5).

Example 3

Assessment of Purity of Final Perlecan Preparations by Silver and Alcian Blue Staining The purity of perlecan that was obtained in the final preparations were evaluated for quality. For these analyses, a combination of silver staining, alcian blue staining and western blotting were employed (as described below) on aliquots of purified perlecan. In order to determine that no significant quantity of other proteins were present in our final perlecan preparations, silver staining of SDS-PAGE gels were first used. For these studies, 6.25 µg aliquots (determined by Lowry) of perlecan were separated on 4–12% gradient SDS-PAGE gels under reducing conditions and stained with silver (see Materials and Methods). As shown in FIG. 4A, perlecan was observed at the resolving gel interface, with no other lower $M_r$ bands present. This observation indicated that our final perlecan preparations did not contain any contaminating proteins with a $M_r$<700–800 kDa (detectable by silver staining).

This same perlecan preparation was then stained with Alcian blue (FIG. 4B) to determine possible contamination by other smaller PGs and/or free GAG chains. As shown in FIG. 4B, lane 1, Alcian blue staining of undigested perlecan demonstrated only one band (indicative of intact perlecan) at the 4–12% gradient SDS-PAGE gel interface. No other Alcian blue stained bands of lower $M_r$ were observed indicating the absence of any other PGs and/or free GAG chains in our final perlecan preparations. To confirm that the high $M_r$ Alcian blue stained material (believed to represent perlecan)(FIG. 4B, lane 1) contained heparan sulfate GAGs, digestion with heparinase/heparitinase (specific for heparan sulfate and/or heparin GAGs) was also used. As shown in FIG. 4B, lane 2, following digestion with heparitinase/heparinase a marked reduction in Alcian blue staining was observed (compare FIG. 4B, lane 2 to lane 1). This indicated that the putative perlecan band (shown in FIG. 4B, lane 1) contained heparan sulfate GAG chains.

Figure 5:
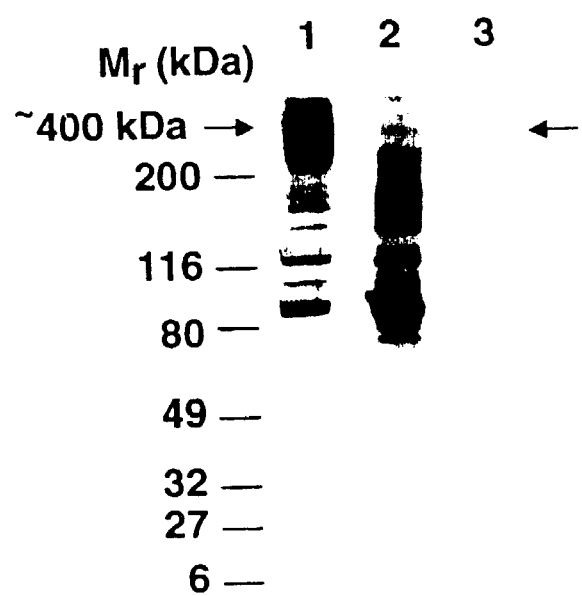
FIG. 5 is a black and white photograph of silver staining of the final perlecan preparations to ensure intact perlecan core protein and absence of any contaminating proteins/proteoglycans.

In order to demonstrate that the Alcian blue and silver stained bands observed at the resolving gel interface in FIG. 4A (lane 1) and 4B (lane 1) were in fact intact perlecan, and that no other proteins or contaminating PGs were present in the final perlecan preparations, heparitinase/heparinase and nitrous acid digested samples of the final perlecan product were also stained with silver (FIG. 5). As shown in FIG. 5, lane 1 (arrow) a discrete doublet characteristic of the perlecan core protein was observed at ~400 kDa by silver staining following heparitinase/heparinase digestion. Silver staining of only the heparitinase/heparinase enzymes employed (in the absence of perlecan)(FIG. 5, lane 2) did not show the characteristic ~400 kDa doublet observed in FIG. 5, lane 1. Nitrous acid digestion of the final perlecan product followed by silver staining also yielded similar results (FIG. 5, lane 3). A characteristic ~400 kDa band indicative of the intact perlecan core protein was observed on silver staining following nitrous acid pretreatment (FIG. 5, lane 3). These studies indicated that no other protein or PG bands were present in the final perlecan preparations, even following liberation of the perlecan core protein by heparitinase/heparinase or nitrous acid.

Example 4

Assessment of Purity of Final Perlecan Preparations by Western Blotting

In order to further demonstrate and confirm the presence of perlecan, and the absence of other basement membrane components produced by the EHS tumor (i.e. laminin, fibronectin and type IV collagen) in the final perlecan preparations, Western blotting with specific antibodies was employed. FIG. 6, lane 1 is a Western blot of our final perlecan preparation following separation oil a 4–12% gradient SDS-PAGE (under non-reducing conditions) probed with a monoclonal antibody against perlecan core protein. As shown, perlecan immunoreactivity was apparent at the resolving gel interface, proving that the positive silver (FIG. 4A) and Alcian blue (FIG. 4B, lane 1) staining observed at the resolving gel interface previously, was in fact intact perlecan core protein. Following heparinase/heparitinase digestion (FIG. 6, lane 2) the perlecan monoclonal antibody detected a doublet at 400 kDa and 360 kDa, characteristic and indicative of intact perlecan core protein (Hassell et al, *J. Biol. Chem.* 260:8098–8105, 1985; Ledbetter et al., *Biochem.* 26:988–995, 1987; Kato et al, *J. Cell Biol.* 106: 2203–2210, 1988).

The purity of the final perlecan preparations were further confirmed by Western blotting and probing with a series of antibodies directed against other basement membrane components known to be produced by the EHS tumor and known to bind to perlecan. As shown in FIG. 6, lane 3, although 1 µg of EHS laminin was strongly stained on Western blot when probed with an anti-laminin antibody (positive control for FIG. 6, lane 4), no positive immunostaining for laminin was observed in 6.25 µg of our final perlecan preparation (FIG. 6, lane 4). Similarly, although 1 µg of fibronectin stained strongly on Western blot when probed with an anti-fibronectin antibody (FIG. 6, lane 5), no positive immunostaining for fibronectin was observed in 6.25 µg of our final perlecan preparation. Furthermore, although 1 µg of type IV collagen stained strongly on Western blot when probed with an anti-type IV collagen antibody (FIG. 6, lane 7), no positive Immunostaining for type IV collagen was observed in 6.25 µg of our final perlecan preparation (FIG. 6, lane 8). These latter studies indicated that only perlecan, and no other basement membrane components produced by the EHS tumor, was present in the final perlecan preparations.

Example 5

Discussion Pertaining to Perlecan Isolation Methodology

The present invention discloses methods for isolation of perlecan from the EHS tumor. The protocol is unique in part in that the method does not require cesium chloride density gradient centrifugation, as has been previously specified by all investigators (Fujiwara et al., *Eur. J. Biochem.* 143: 145–157, 1984; Hassell et al, *J. Biol. Chem.* 260:8098–8105, 1985; Ledbetter et al., *Biochem.* 26:988–995, 1987; Paulsson et al., *J. Mol. Biol.* 197:297–313, 1987; Kato et al, *J. Cell Biol.* 106:2203–2210, 1988). The perlecan product obtained by our protocol was of high quality and did not contain any contaminants produced by the EHS tumor, including other basement membrane components (i.e. laminin, fibronectin, and type IV collagen)(assessed by silver staining and Western blotting with specific antibodies) and/or free GAG chains (assessed by Alcian blue staining). The presence of contaminating basement membrane proteins (especially laminin) in perlecan preparations has posed a major problem in the past, and it is essential that the perlecan used for in vitro and/or in vivo studies be thoroughly analyzed for components which can potentially interact with perlecan during the isolation procedure. In the present invention, a detailed perlecan isolation procedure employed for consistent production of high quality perlecan is described. In addition, the quality control steps employed to ensure the production of an essentially clean perlecan product are disclosed.

Comparison to known Perlecan Isolation Methods

Isolation of perlecan has been previously described by several investigators (Fujiwara et al., *Eur. J. Biochem.* 143:145–157, 1984; Hassell et al, *J. Biol. Chem.* 260: 8098–8105, 1985; Ledbetter et al., *Biochem.* 26:988–995, 1987; Paulsson et al., *J. Mol. Biol.* 197:297–313, 1987; Kato et al, *J. Cell Biol.* 106:2203–2210, 1988). In one previous study (Hassell et al, *J. Biol. Chem.* 260:8098–8105, 1985), perlecan was isolated from EHS tumor initially using non-denaturing conditions (extraction with buffered saline), followed by denaturing conditions (extraction with urea). The urea extracts were then processed utilizing DEAE-Sephacel chromatography, followed by ultracentrifugation, dialysis, gel filtration chromatography (Sepharose CL-4B), exhaustive dialysis and lyophilization. One of the problems noted by the authors in the above procedure (Hassell et al, *J. Biol Chem.* 260:8098–8105, 1985) was the contaminating presence of laminin and other proteins, believed to be inherently bound to perlecan by disulfide-dependent association, which could only be removed by disulfide bond reduction (using dithiothreitol) followed by ion exchange chromatography. In another study, increased purity was achieved when the protocol was modified by pre-extracting the tumor tissue with 3.4 M NaCl before extraction with 6M urea (Ledbetter et al., *Biochem.* 26:988–995, 1987). However, this latter method resulted in occasional partial degradation of the large 400 kDa perlecan core protein (Paulsson et al., *J. Mol. Biol.* 197:297–313, 1987).

Extraction of EHS tumor with chaotrophic agents such as 4M guanidine-HCl allowed for rapid and efficient extraction of PGs (Hassell et al., *Proc. Natl. Acad. Sci.* 77:4494–4498, 1980; Kato et al., *J. Biol. Chem.* 262:7180–7188, 1987; Kato et al, *J. Cell Biol.* 106:2203–2210, 1988) and is the preferred extraction protocol for the invention, although others may be made to serve as well. The denaturing conditions and the use of protease inhibitors in the extraction solution protect the integrity of the large perlecan core protein (see FIG. 2, lane 1), which is susceptible to proteolysis (Paulsson et al., *J. Mol. Biol.* 197:297–313, 1987). It is calculated that >90% of GAGs (as determined by an Alcian blue assay) (Björnson, *Anal. Biochem.* 210:282–291, 1993) were extracted from EHS tumor tissue using 4M guanidine-HCl containing 0.5% CHAPS and protease inhibitors (not shown).

However, in addition to the presence of PGs, the guanidine extracts contained large amounts of non-PG proteins which may potentially interfere with subsequent ion-exchange chromatography. Gel filtration chromatography using a Sephacryl S-400 column allowed for both buffer exchange (7M urea with detergent and protease inhibitors) and the removal of a large number of small molecular weight proteins (compare FIG. 2, lane 2 to lane 1) which could not be accomplished by a much longer dialysis process, contrary to what has been previously suggested (Kato et al., *J. Biol. Chem.* 262:7180–7188, 1987; Hassell et al, *J. Biol. Chem.* 260:8098–8105, 1985). The guanidine-HCl extract from 50 grams of EHS tumor (~400 ml) was exchanged into 7M urea buffer (described above) in less than one day, requiring less than 3 liters of buffer.

Yield of Perlecan

The final yield of perlecan using the method of the invention was approximately 10–12.5 µg per gram of EHS tumor wet weight, as measured by protein determination (Hassell et al., *Proc. Natl. Acad. Sci.* 77:4494–4498, 1980). Although clonal differences in EHS tumor may result in variations in GAG chain length (Paulsson et al., *J. Mol. Biol.* 197:297–313, 1987), a protein to GAG ratio of approximately 1:1 in our purified perlecan product was calculated (not shown). This is similar to GAG:protein ratios of the low density HSPG (i.e. perlecan) previously described by Fujiwara et al (*Eur. J. Biochem.* 143:145–157, 1984). Additionally, the total GAG content present in the EHS tumor tissue determined by using an Alcian blue assay (Björnson, *Anal. Biochem.* 210:282–291, 1993), was approximately 0.90 mg of GAGs per gram wet weight of EHS tumor (not shown). This is greater than the 0.75 mg of GAGs per gram wet weight of EHS tumor previously reported by Fujiwara et al (*Eur. J. Biochem.* 143:145–157, 1984). Following S-1000 fractionation, only 20% (150–180 µg per gram tumor wet weight) of the calculated GAG content was found to be attributed by perlecan, consistent with the study by Dziadek et al (*EMBO J* 4:905–912, 1985), whereas most of the remaining GAG content was present in the 220 kDa PG (not shown). Based on these determinations, the final perlecan yield using the described protocol from starting EHS tumor tissue was approximately 10%. Two hundred grams of EHS tumor consistently yields approximately 3–4 mg of perlecan.

Example 6

Identification of an Aggregating ~220 kDa PG which can be Separated from Perlecan Earlier studies have demonstrated two major PGs to be produced by the EHS tumor (Fujiwara et al., *Eur. J. Biochem.* 143:145–157, 1984; Dziadek et al., *EMBO J.* 4:905–912, 1985; Kato et al., *J. Biol. Chem.* 262:7180–7188, 1987; Hassell et al, *J. Biol. Chem.* 260: 8098–8105, 1985; Ledbetter et al., *Biochem.* 26:988–995, 1987). Based on cesium chloride density gradient centrifugation they were designated as a high density HSPG ($\geq 1.65$ g/ml) and a low density HSPG (1.38 g/ml)(Kato et al., *J. Biol. Chem.* 262:7180–7188, 1987; Hassell et al, *J. Biol. Chem.* 260:8098–8105, 1985; Ledbetter et al., *Biochem.* 26:988–995, 1987). The low density HSPG was later found to be analogous to perlecan, whereas the high density HSPG had an electrophoretic mobility of 200–400 kDa (Fujiwara et al., *Eur. J. Biochem.* 143:145–157, 1984), and was postulated to represent either a breakdown product of the low density HSPG (i.e. perlecan)(Hassell et al, *J. Biol. Chem.* 260:8098–8105, 1985; Ledbetter et al., *Biochem.* 26:988–995, 1987), or an independent PG derived from a separate gene product (Kato et al., *J. Biol. Chem.* 262: 7180–7188, 1987; Paulsson et al., *J. Mol. Biol.* 197:297–313, 1987). Although these latter possibilities have not been fully resolved, the high density HSPG previously identified by cesium chloride centrifugation is most likely identical to the 220 kDa PG described herein. This 220 kDa PG, like the known high density HSPG (Kato et al., *J. Biol. Chem.* 262:7180–7188, 1987; Hassell et al, *J. Biol. Chem.* 260:8098–8105, 1985; Ledbetter et al., *Biochem.* 26:988–995, 1987), was found to be the major PG extractable by saline and contained heparan sulfate GAG chains as demonstrated by degradation with heparinase/heparitinase digestion (not shown).

One of the unique discoveries of the present invention is that under certain chromatographic conditions, the 220 kDa PG self-aggregates, which enables it to be separated from perlecan (which itself did not aggregate under similar conditions). These differences in aggregating properties allowed us to develop a novel method to purify perlecan without contamination by the 220 kDa PG, using Sephacryl S-1000 chromatography. The self-aggregating property of the 220 kDa PG appeared not to involve any other proteins as determined by analysis of SDS-PAGE gels by silver staining (not shown). The 220 kDa PG eluted from the Sephacryl S-1000 in the void volume (see FIG. 3) indicating that this PG formed large aggregates of >>100,000 kDa, which occurred even under dissociating conditions.

Example 7

Further Improved Protocol for Perlecan Isolation from EHS Tumor

Figure 7:
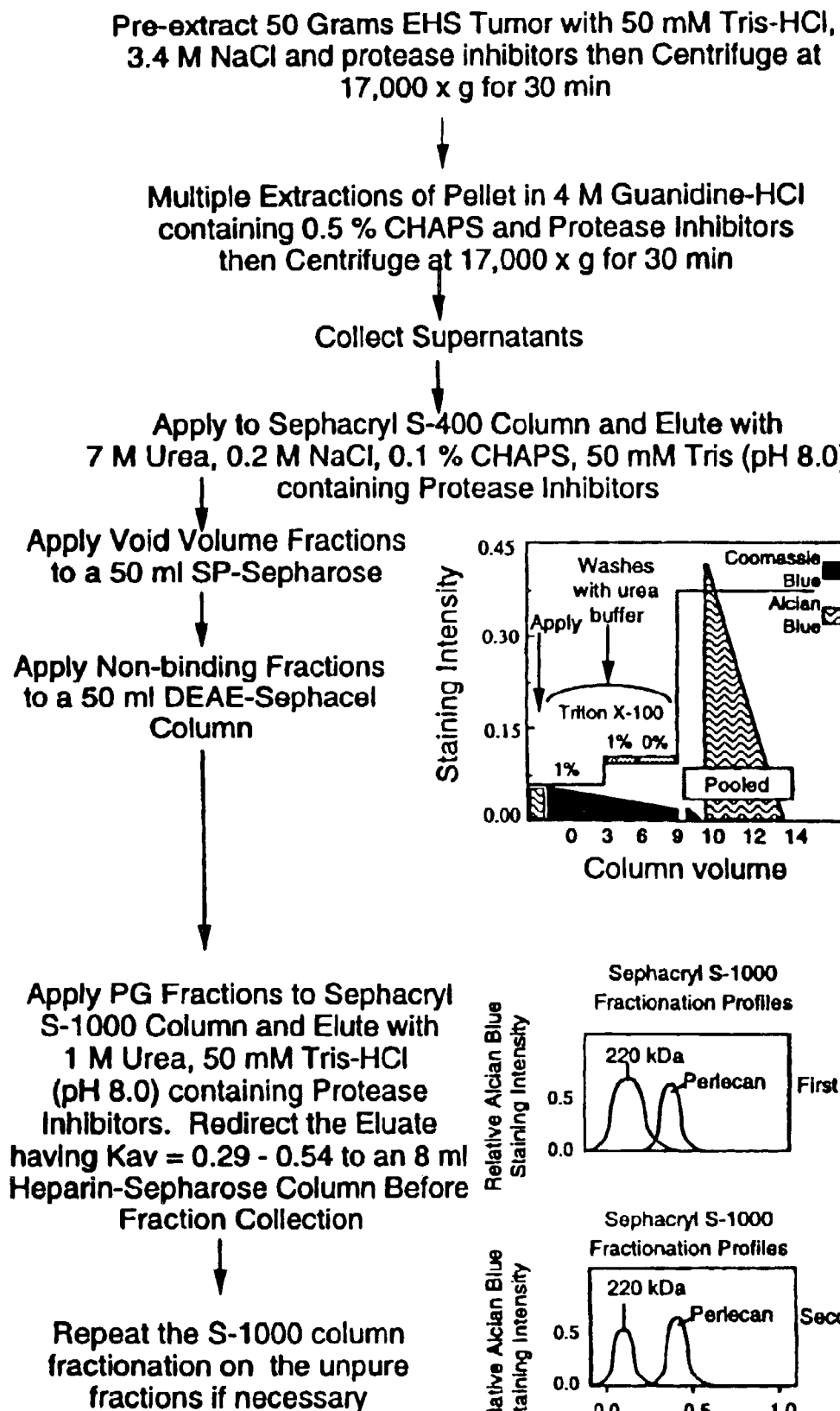
FIG. 7 is a schematic describing another protocol employed for perlecan purification from the Engelbreth-Holm-Swarm tumor with further modification steps to improve both clean perlecan yield, and the time required for isolation.

FIG. 7 describes an alternate protocol used for perlecan isolation from the EHS tumor, which contains two additional steps which both further improve perlecan yield and reduce the number of passes required for Sephacryl S-1000 chromatography.

The first improvement to the method disclosed in detail in Examples 1–4, is the use of a Sulphopropyl Sepharose (SP)

column, a cationic exchange column which is also effective in removing any contaminating proteins which may interact with perlecan during the isolation procedure. For this step, the void volume fractions (believed to contain perlecan) from the Sephacryl S-400 column are pooled and supplemented with 0.5% Triton X-100 (v/v) and applied to a 50 ml Sulphopropyl Sepharose (SP) column (Pharmacia) packed in a 60 ml plastic syringe. The eluates are then applied to the 50 ml DEAE-Sephacel column and follow the corresponding procedure as detailed in Examples 1–4. It is an aspect of the invention that cationic exchange columns (i.e. anionic resins) such as DEAE-Sephacel can be employed to clean up PG extracts by removing unwanted proteins or macromolecules which associate with the PGs in vivo and/or during the isolation procedure.

A second improvement to the method disclosed in Examples 1–4 is the use of a heparin-Sepharose column which is also effective in removing possible contaminating laminin, fibronectin, and/or type IV collagen, all of which interact with perlecan during the isolation procedure. For this step, PGs eluted from DEAE-Sephacel are precipitated with 4 volumes of methanol containing 2.5% (w/v) sodium acetate by cooling on dry ice for 1 hour and then centrifuging at 17,000×g for 20 minutes. The pellet is redissolved in 50 ml of 1M urea buffer (containing 50 mM Tris-HCl and protease inhibitors including 1.4 mM EDTA, 1.4 mM NEM, 1.4 mM 6-aminohexanoic acid, 0.7 mM benzamidine, and 0.14 mM PMSF; pH 8.0) and loaded onto the Sephacryl S-1000 column (as described in Examples 1–4). The eluate containing perlecan ($K_{av}$=0.29–0.54) is redirected through an 8 ml heparin-Sepharose column (Pharmacia) before going to the fraction collector. The fractions were then monitored by SDS-PAGE analysis in order to access the purity of the perlecan and other heparan sulfate PGs which may be present.

For this latter analysis, 100 µl aliquots of each of 60 ml fractions were precipitated with 4 volumes of absolute ethanol containing 2.5% (w/v) sodium acetate by cooling on dry ice for 1 hour, centrifuged on a microcentrifuge at 12,000×g for 20 minutes, and run on SDS-PAGE. Fractions containing high quality perlecan free from any other contaminating HSPGs (i.e. 220 kDa PG) or other PGs were pooled and precipitated as above. Fractions containing perlecan with other contaminants were also precipitated and passed through a smaller Sephacryl S-1000 column (2.6×60 cm) for a second time (as described above). The resulting pellets containing "clean" perlecan were dissolved in 3–5 ml of double distilled water and extensively dialyzed against double distilled water until the conductivity of the end product contained very little to no salt (2–3 µmhos) as measured using a digital conductivity meter. The final perlecan product was then freeze-dried and stored. The final purity of the perlecan preparations were further assessed by Alcian blue staining, Coomassie blue staining, silver staining, and a series of Western blots (as described in sections 4.2.2–4.2.5).

Columns containing immobilized GAGs (such as heparin Sepharose) in an affinity type column chromatography can also be advantageously used to "clean" up PG preparations. For example, a Sepharose column containing immobilized chondroitin sulfate may be used for the isolation of chondroitin sulfate containing PGs from tissues and/or cell culture. Using this methodology, chondroitin sulfate binding proteins or macromolecules will bind to the chondroitin sulfate column when passed through, allowing for "cleaner" preparations of the resulting chondroitin sulfate PGs/GAGs which follow through the column. These columns containing immobilized GAGs may also be advantageously used in large scale for isolation of different types and/or classes of PGs/GAGs for commercial utilities.

Using these two modifications as described above, 200 grams of EHS tumor wet weight has a perlecan yield in the range of 4–5 mg (as compared to 3–4 mg using the protocol described in Examples 1–4). In addition, only 2 passes through the Sephacryl S-1000 column (instead of three) are required to obtain "clean" perlecan.

Example 8

Use of the Perlecan Product in a Rat Infusion Model

The clean perlecan and HSPG products obtained from the methodology described in the present invention can then be advantageously used to produce a significantly more consistent and more reliable animal model with which to study fibrillar amyloid, and in particular Aβ amyloid, deposition/persistence in brain than has previously been possible with less pure product. These improved animal models can also be used to screen and identify new therapeutic agents which target fibrillar Aβ deposition, accumulation, and/or persistence. As an example to demonstrate the utility of clean perlecan the following study was implemented.

For rat animal model studies, Aβ (residues 1–40: lot #WM365; Bachem California Inc., Torrance, Calif.) was initially dissolved in double distilled sterile water at a concentration of 1 mg/ml (stock solution). 50 µl of Aβ stock solutions were then transferred with sterile pipettes to microcentrifuge tubes containing either 50 µl of sterile distilled water, or 25 µg of perlecan recently dissolved in 50 µl of distilled sterile water. The Aβ (1–40), and Aβ (1–40)+perlecan solutions were then either frozen at −70° C. or used immediately in the animal model (described below).

20 male Harlan Sprague-Dawley rats (250–300 g; 3 months old) were anesthetized with pentobarbital (50 mg/kg) and a 27 gauge stainless steel cannula was stereotactically implanted into the hippocampus using bregma as reference point (AP −4.8; ML 3.5; DV 3.0) and secured to the skull by machine screws and dental acrylic. The cannula was connected via a 15 cm coil of vinyl tubing to a model 2002 osmotic minipump (Alzet Inc.) placed subcutaneously beneath the shoulder blades. The infused solution was contained entirely within the coil of vinyl tubing and separated from water in the pump (dyed blue with food coloring) by a 3 cm air spacer. Successful performance of the pumps was confirmed by measuring movement of the air spacer and blue saline solution following sacrifice. In the present study to demonstrate the effects of isolated EHS perlecan in this animal model, 10 animals received infusion of either Aβ (1–40) only, or Aβ (1–40)+Perlecan, directly into hippocampus at a flow rate of 0.5 µl/hr for 1 week. A high concentration of Aβ was chosen to maximize possible effects following infusion into brain. The quantity of Aβ peptide infused into brain by the end of 1 week in each animal was approximately 50 µg.

Rats were sacrificed by an overdose of pentobarbital and perfused with 100 ml of saline followed by 150 ml of 4% paraformaldehyde buffered with phosphate (pH 7.4), the brains were removed and postfixed for 48 hr, and transferred to PBS for frozen tissue sectioning. Consecutive 25 µm serial sections were cut using a sliding microtome and placed on gelatin-coated slides.

As we previously described (Snow et al., *Neuron* 12:219–234, 1994), detection of infused Aβ was monitored using a polyclonal antibody against synthetic Aβ or a monoclonal antibody (6E10; Senetek) which recognizes residues 1–17 of Aβ. Perlecan accumulation was monitored using a polyclonal antibody against the core protein of perlecan. From each animal, 100 consecutive serial sections were cut and stained with cresyl violet to identify the area occupied by the infusion site. Usually, the infusion site spanned 40–60 serial sections. Congo red staining (Puchtler et al., *J. Histochem. Cytochem.* 10:355–364, 1962) and Thioflavin S fluorescence (Elghetany and Saleem, *Stain Tech.* 63:201–212, 1988) were then used on every 10th section spanning through the entire infusion site to determine the extent and consistency of possible fibrillar Aβ amyloid deposition in these animals. The percent of animals containing congophilic deposits (indicative of fibrillar amyloid) in each of the two groups was assessed by blind scoring of tissue sections (scoring of every 10th congo red stained sections through the entire infusion site) using an arbitrary scale of scoring (from 0 to 5) as previously described (Snow et al., *Neuron* 12:219–234, 1994). Tissue sections with the anti-Aβ antibodies were pretreated for 3–5 minutes with 88% formic acid before immunostaining to aid in unmasking hidden antigenic sites as previously reported (Kitamoto et al., *Lab. Invest.* 57:230–236, 1987). For immunostaining, negative controls consisted of using TBS instead of the primary antibody and/or preabsorption experiments using the primary antibody in the presence of excess antigen (Snow et al., *Am. J. Path.* 137:1253–1270, 1990).

Results of Aβ only Versus Aβ+Perlecan Infusion Into Rodent Brain

High quality "clean" perlecan is believed to be essential to establish a consistent and reproducible animal model to study the effects of fibrillar Aβ amyloid deposits in rodent brain. Following a 1 week-infusion of Aβ (1–40) alone, or Aβ (1–40)+clean perlecan into rodent hippocampus, it was evident that differences between the two groups existed in the extent and percent of animals with Aβ fibrillar amyloid deposits. 100% (10 of 10) of animals infused with Aβ (1–40)+clean perlecan for 1 week demonstrated Congo red and Thioflavin S-positive deposits (indicative of amyloid) at the infusion site (FIG. 8). In comparison only 60% (6 of 10) of animals infused with Aβ (1–40) alone demonstrated Congo red or Thioflavin S-positive deposits at the infusion site. The Congo red (not shown) and Thioflavin S (FIG. 8B) positive deposits in the Aβ+perlecan group corresponded on adjacent serial sections to precisely those areas containing both Aβ (FIG. 8B) and perlecan (not shown), as previously demonstrated (Snow et al., *Neuron* 12:219–234, 1994). This in vivo study therefore demonstrated that consistent fibrillar Aβ deposition and persistence could be obtained with the use of a high quality perlecan product (in the presence of Aβ 1–40).

Our studies utilizing this animal model suggest that the final purity of the perlecan preparation is essential, if not critical, for continued reliability of fibrillar Aβ amyloid deposition and persistence in brain. Contaminating proteins such as laminin, fibronectin and type IV collagen, which are produced by the EHS tumor and which normally associate with perlecan can cause unexpected variability in the animal model (Snow, Cummings and Castillo, unpublished observations). Other investigators who attempt to replicate these findings with the described rodent model must ensure that the perlecan used is of the highest quality and "free" of contaminating proteins, as described in the present invention. Even the presence of free GAG chains (i.e. heparan sulfate) in perlecan preparations will compete with perlecan for binding sites on Aβ and will disrupt the consistency of this animal model (Snow and Castillo, unpublished observations).

Further Aspects and Utilizations of the Invention

One aspect of the present invention is to provide methods for the consistent production of "clean" and "non-contaminated" perlecan for use in a number of different and relevant in vitro and in vivo biological assays as described herein.

Improved Methodologies to Isolate Substantially "Pure" Proteoglycans

In our methodology a cationic exchange column (i.e. anionic resin) was used and found effective in removing any contaminating proteins which may interact with perlecan during the isolation procedure. For our protocol, we used a 50 ml Sulphopropyl Sepharose (SP) column (Pharmacia) packed in a 60 ml plastic syringe. Cationic exchange columns may be employed to clean up any PG extracts by removing unwanted proteins or macromolecules which associate with the PGs in vivo and/or during the isolation procedure. Such strong cationic-exchange resins can be purchased from Pharmacia Biotech (USA) and include columns containing: 1) Mini S (minibeads), 2) Mono S (monobeads), 3) Source 15S (prepacked columns), 4) Source 30S (lab packs), 5) SP Sepharose High Performance, and 6) SP Sepharose Fast Flow. Other anionic resins obtained from other companies may also be useful.

Another improvement to our isolation methodology was the use of a heparin-Sepharose column which was effective in removing possible contaminating laminin, fibronectin, and/or type IV collagen, all of which interact with perlecan during the isolation procedure. For this step in the isolation protocol, the eluate containing perlecan ($K_{av}$=0.29–0.54) was re-directed through an 8 ml heparin-Sepharose column (Pharmacia) before going to the fraction collector. Columns containing immobilized GAGs (such as heparin Sepharose) can be also used to "clean" up other types of PG preparations. For example, a Sepharose column containing immobilized chondroitin sulfate may be useful for the isolation of chondroitin sulfate containing PGs from tissues and/or cell culture. Using this methodology, chondroitin sulfate binding proteins or macromolecules, will bind to the chondroitin sulfate column when passed through, allowing for "cleaner" preparations of the chondroitin sulfate PGs/GAGs which will flow through the column. Similarly, Sepharose columns containing immobilized dermatan sulfate, keratan sulfate, or heparan sulfate may also be used to aid in the isolation of dermatan sulfate PGs, keratan sulfate PGs and heparan sulfate PGs, respectively. These and other immobilized-GAG columns may also be used in large scale for isolation of different types and/or classes of PGs/GAGs for commercial utilities.

Antibodies

One aspect of the present invention is to use perlecan or the ~220 kDa HSPG obtained by the described isolation protocols described herein, to produce new polyclonal and/or monoclonal antibodies. Antibodies generated against "clean" perlecan or the ~220 kDa HSPG, isolated as described herein, can be obtained by direct injection into an animal or by administering to an animal, preferably a nonhuman.

The term "antibody" is meant to include polyclonal antibodies, monoclonal antibodies, chimeric antibodies, anti-idiotypic antibodies to antibodies specific for perlecan or the ~220 kDa HSPG of the present invention.

Polyclonal antibodies are heterogeneous populations of antibody molecules derived from the sera of animals immunized with an antigen.

A monoclonal antibody contains a substantially homogeneous population of antibodies specific to antigens, which population contains substantially similar epitope binding sites. For preparation of monoclonal antibodies, any technique which provides antibodies produced by continuous cell line cultures can be used. Examples include the hybridoma technique (Kohler and Milstein, *Nature* 256:495–497, 1975), the trioma technique, the human B-cell hybridoma technique (Kozbor et al, *Immunology Today* 4:72, 1983), and the EBV-hybridoma technique to produce human monoclonal antibodies (Cole et al, in *Monoclonal Antibodies and Cancer Therapy,* Alan R. Liss, Inc., pp. 77–96, 1985). Such antibodies may be of any immunoglobulin class including IgG, IgM, IgE, IgA, GILD and any subclass thereof.

Chimeric antibodies are molecules different portions of which are derived from different animal species, such as those having variable region derived from a murine monoclonal antibody and a human immunoglobulin constant region, which are primarily used to reduce immunogenicity in application and to increase yields in production. Chimeric antibodies and methods for their production are known in the art (ex. Cabilly et al, *Proc. Natl. Acad. Sci. U.S.A.* 81:3273–3277, 1984; Harlow and Lane: *Antibodies: A Laboratory Manual,* Cold Spring Harbor Laboratory 1988).

An anti-idiotypic antibody is an antibody which recognizes unique determinants generally associated with the antigen-binding site of an antibody. An anti-idiotypic antibody can be prepared by immunizing an animal of the same species and genetic type (e.g., mouse strain) as the source of the monoclonal antibody with the monoclonal antibody to which an anti-idiotypic antibody is being prepared. The immunized animal will recognize and respond to the idiotypic determinants of the immunizing antibody by producing an antibody to these idiotypic determinants (the anti-idiotypic antibody). See, for example, U.S. Pat. No. 4,699,880, which is herein incorporated by reference.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al, *J. Nucl. Med.* 24:3 16–325, 1983).

The antibodies or fragments of antibodies, useful in the present invention may be used to quantitatively or qualitatively detect perlecan, perlecan-derived fragments or the ~220 kDa HSPG (and its fragments) in a sample or to detect presence of cells which express perlecan or the ~220 kDa HSPG. This can be accomplished by immunofluorescence techniques employing a fluorescently labeled antibody coupled with light microscopic, flow cytometric or fluorometric detection.

One of the ways in which a perlecan, perlecan-fragment or ~220 kDa HSPG antibody can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorometric, or by visual means. Enzymes which can be used detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colometric methods which employ a chromogenic substrate for the enzyme. Detection can be accomplished by colometric methods which employ a chromogenic substrate for the enzyme. Detection can also be accomplished by visual comparison of the extent of enzymatic reaction of a substrate with similarly prepared standards (see Harlow and Lane, *Antibodies: A Laboratory Manual,* Cold Spring Harbor Laboratory 1988; Ausubel et al, eds., *Current Protocols in Molecular Biology,* Wiley Interscience, N.Y. 1987, 1992).

Detection may be accomplished using any of a variety of other immunoassays. For example, by radiolabeling of the antibodies or antibody fragments, it is possible to detect R-PTPase through the use of a radioimmunoassay (RIA). A good description of RIA may be found in *Laboratory Techniques and Biochemistry in Molecular Biology,* by Work et al, North Holland Publishing Company, NY (1978) with particular reference to the chapter entitled "An Introduction to Radioimmune Assay and Related Techniques" by Chard, incorporated entirely by reference herein. The radioactive isotope can be detected by such means as the use of a gamma-counter, a scintillation counter or by autoradiography.

It is also possible to label perlecan, perlecan fragments, the ~220 kDa HSPG, or ~220 kDa HSPG-fragments described herein, with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine, commercially available, e.g., from Molecular Probes, Inc. (Eugene, Oreg., U.S.A.).

The antibody can also be detectably labeled using fluorescence emitting metals such as $^{152}$EU, or other of the lanthanide series. These metals can be attached to the antibody using such metal groups as diethylenetriamine pentaacetic acid (EDTA).

The antibody can also be detectably labeled by coupling it to a chemiluminescent compound. The presence of the chemiluminescent-tagged antibody is then determined by detecting the presence of luminescence that arises during the course of a chemical reaction, Examples of particularly useful chemiluminescent labeling compounds are luminol, isoluminol, theromatic acridinium ester, imidazole, acridinium salt, and oxalate ester.

Likewise, a bioluminescent compound may be used to label the antibody of the present invention. Bioluminescence is a type of c hemiluminescence found in biological systems in which a catalytic protein increases i;he efficiency of the chemiluminescent reaction. The presence of a bioluminescent protein is determined by detecting the presence of luminescence. Important bioluminescent compounds for purposes of labeling are luciferin, luciferase and aequorin.

The antibodies (or fragments thereof) useful in the present invention may be employed histologically, as in immunofluorescence or immunoelectron microscopy, for in situ detection of perlecan, perlecan fragments, the ~220 kDa HSPG or ~220 kDa HSPG fragments, of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of perlecan, perlecan fragments, the ~220 kDa HSPG or ~220 kDa HSPG fragments, but also its distribution on the examined tissue. Using the present invention, those of ordinary skill will readily perceive that any of a wide variety of histological methods (such as staining procedures) can be modified in order to achieve such in situ detection.

In accordance with yet a further aspect of the present invention there are provided antibodies against perlecan, perlecan fragments, the ~220 kDa HSPG or a ~220 kDa HSPG-fragments. These antibodies can be used for a number of important diagnostic and/or therapeutic applications as described herein. In one aspect of the invention, polyclonal and/or monoclonal antibodies made against perlecan, perlecan fragments, the ~220 kDa HSPG or ~220 kDa HSPG fragments may be used for Western blot analysis (using standard Western blotting techniques knowledgeable to those skilled in the art) to detect the presence of amyloid protein-binding perlecan fragments or amyloid protein-binding ~220 kDa HSPGs in human tissues and in tissues of other species. Western blot analysis can also be used to determine the apparent size of each amyloid protein-binding perlecan or amyloid protein-binding ~220 kDa HSPG fragments. In addition, Western blotting following by scanning densitometry (known to those skilled in the art can be used to quantitate and compare levels of each of the perlecan or ~220 kDa HSPG fragments in tissue samples, biological fluids or biopsies obtained from individuals with specific diseases (such as the amyloid diseases) in comparison to tissue samples, biological fluids or biopsies obtained from normal individuals or controls. Biological fluids, include, but are not limited to, blood, plasma, serum, cerebrospinal fluid, sputum, saliva, urine and stool.

In yet another aspect of the invention, polyclonal and/or monoclonal antibodies made against perlecan, perlecan fragments, the ~220 kDa HSPG or ~220 kDa HSPG-fragments can be used for immunoprecipitation studies (using standard immunoprecipitation techniques known to one skilled in the art) to detect perlecan, perlecan fragments, the ~220 kDa HSPG or ~220 kDa HSPG-fragments which bind Aβ or other amyloid proteins, in tissues, cells and/or biological fluids. Use of the perlecan, perlecan fragments, the ~220 kDa HSPG or ~220 kDa HSPG-fragment antibodies for immunoprecipitation studies can also be quantitated to determine relative levels of perlecan, perlecan fragments, the ~220 kDa HSPG or ~220 kDa HSPG-fragments which interact with Aβ or other amyloid proteins, in tissues, cells and/or biological fluids. Quantitative immunoprecipitation can be used to compare levels of perlecan, perlecan fragments, the ~220 kDa HSPG or ~220 kDa HSPG-fragments in tissue samples, biological fluids or biopsies obtained from individuals with specific diseases (such as the amyloid diseases) in comparison to tissue samples, biological fluids or biopsies obtained from normal individuals or controls.

Diagnostic Applications

Use of Perlecan, ~220 kDa HSPG and/or Antibodies

Another aspect of the invention is to provide polyclonal and/or monoclonal antibodies to perlecan, perlecan fragments, the ~220 kDa HSPG or ~220 kDa HSPG-fragments which would be used to specifically detect perlecan, perlecan fragments, the ~220 kDa HSPG or ~220 kDa HSPG-fragments in human tissues and/or biological fluids. In one preferred embodiment, polyclonal or monoclonal antibodies made against clean perlecan, perlecan fragments, the ~220 kDa HSPG or ~220 kDa HSPG-fragments, can be used to detect and quantify perlecan, perlecan fragments, the ~220 kDa HSPG or ~220 kDa HSPG-fragments in human tissues and/or biological fluids. For detection of perlecan, perlecan fragments, the ~220 kDa HSPG or ~220 kDa HSPG-fragments in human tissues, cells, and/or in cell culture, the polyclonal and/or monoclonal antibodies can be used using standard immunohistochemical and immunocytochemical techniques, knowledgeable to one skilled in the art.

For detection and quantitation of perlecan, perlecan fragments, the ~220 kDa HSPG or ~220 kDa HSPG-fragments in biological fluids, including plasma, serum, urine, cerebrospinal fluid, sputum, and/or stool, various types of ELISA assays can be used, knowledgeable to one skilled in the art. In a preferred embodiment, a sandwich type of ELISA can be used. Using this preferred method a pilot study is first implemented to determine the quantity of binding of a clean perlecan, perlecan fragment, ~220 kDa HSPG or ~220 kDa HSPG-fragment monoclonal antibody to microtiter wells. Once this is determined, aliquots (usually in 40 μl of TBS; pH 7.4) of the antibody are allowed to bind overnight to microtiter wells (Maxisorb C plate from Nunc) at 4° C. A series of blank wells not containing any primary perlecan, perlecan fragment, ~220 kDa HSPG or ~220 kDa HSPG-fragment specific monoclonal antibody are also used as controls. The next day, non-bound monoclonal antibody is shaken off the microtiter wells. All of the microtiter wells (including the blank wells) are then blocked by incubating for 2 hours with 300 μl of Tris-buffered saline containing 0.05% Tween-20 (TTBS) plus 2% bovine serum albumin, followed by 5 rinses with TTBS. 200 μl of plasma, serum, urine, cerebrospinal fluid, sputum, and/or stool and/or any other type of biological sample is then diluted (to be determined empirically) in TTBS containing 2% bovine serum albumin and placed in wells (in triplicate) containing bound perlecan, perlecan fragment, ~220 kDa HSPG or ~220 kDa HSPG-fragment antibody (or blank) and incubated for 2 hours at room temperature. The wells are then washed 5 times with TTBS. A second biotinylated-polyclonal antibody against perlecan, perlecan fragments, the ~220 kDa HSPG or ~220 kDa HSPG-fragments is then added to each well (usually in 40 μl of TBS; pH 7.4) and allowed to bind for 2 hours at room temperature to any perlecan, perlecan fragments, ~220 kDa HSPG or ~220 kDa HSPG-fragments captured by the first antibody. Following incubation, the wells are washed 5 times with TTBS. Bound materials are then detected by incubating with 100 μl of peroxidase-avidin complex (1:250 dilution in TTBS with 0.1% BSA) for 1 hour on a rotary shaker. After 5 washes with TTBS, a substrate solution (100 μl, OPD-Sigma Fast from Sigma Chemical Co., St. Louis, Mo., USA) is added and allowed to develop significant color (usually 8–10 minutes). The reaction is stopped with 50 μl of 4N sulfuric acid and read on a standard spectrophotometer at 490 nm. This ELISA can be used to determine differences in perlecan, perlecan fragments, the ~220 kDa HSPG or ~220 kDa HSPG-fragments levels in biological fluids which can serve as diagnostic markers to follow the progression on a live patient during the progression of disease (i.e. monitoring of amyloid disease as an example). In addition, quantitative changes in perlecan, perlecan fragment, ~220 kDa HSPG or ~220 kDa HSPG-fragments levels can also serve as prognostic indicators monitoring how a live patient will respond to treatment which targets a given amyloid disease.

A competition assay may also be employed wherein antibodies specific to clean perlecan, perlecan fragments, the ~220 kDa HSPG or ~220 kDa HSPG-fragments are attached to a solid support and labeled perlecan, perlecan fragments, the ~220 kDa HSPG or ~220 kDa HSPG-fragments and a sample derived from a host are passed over the solid support and the amount of label detected attached to the solid support can be correlated to the quantity of perlecan, perlecan fragments, the ~220 kDa HSPG or ~220 kDa HSPG-fragments in the sample, all as otherwise is known to those skilled in the art.

Another object of the present invention is to use clean perlecan or fragments thereof, in conjunction with perlecan specific antibodies, in an ELISA assay to detect potential perlecan autoantibodies in human biological fluids. In a preferred embodiment, perlecan will be used to initially bind to microtiter wells in an ELISA plate. A pilot study is first implemented to determine the quantity of binding of perlecan to microtiter wells. Once this is determined, aliquots (usually 1–2 µg in 40_l of TBS; pH 7.4) of perlecan or fragments thereof are allowed to bind overnight to microtiter wells (Maxisorb C plate from Nunc) at 4° C. All the microtiter wells (including blank wells without perlecan) are blocked by incubating for 2 hours with 300 µl of Tris-buffered saline (pH 7.4) with 0.05% Tween-20 (TTBS), containing 2% albumin. This is followed by 5 rinses with TTBS. The patient's biological fluids (ie, plasma, serum, cerebrospinal fluid, sputum, urine, and/or stool) are then used and 200 µl are diluted (to be determined empirically) with TTBS containing 2% bovine serum albumin, and placed in microtiter wells (in triplicate) containing perlecan or blank wells (which do not contain perlecan), and are incubated al 1.5 hours at room temperature. Any autoantibodies present in the biological fluids against perlecan will bind to the substrate bound perlecan (or fragments thereof. The wells are then rinsed by washing 5 times with TTBS. 100 µl of biotinylated polyclonal goat anti-human IgGs (Sigma Chemical company, St. Louis, Mo., USA), diluted 1:500 in TTBS with 0.1% bovine serum albumin, is then aliquoted into each well. Bound materials are detected by incubating with 100 µl of peroxidase-avidin complex (1:250 dilution in TTBS with 0.1% bovine serum albumin) for 1 hour on a rotary shaker. Following 5 washes with TTBS, substrate solution (100 µl, OPD-Sigma Fast from Sigma Chemical Company, St. Louis, Mo., USA) is added and allowed to develop significant color (usually 8–10 minutes). The reaction is stopped with 50 µl of 4N sulfuric acid added to each well and read on a standard spectrophotometer at 490 nm. This assay system can be used to not only detect the presence of autoantibodies against perlecan in biological fluids, but also to monitor the progression of disease by following elevation or diminution of perlecan autoantibody levels. It is believed that patients demonstrating excessive perlecan formation, deposition, accumulation and/or persistence as observed in the amyloid diseases, will also carry autoantibodies against perlecan in their biological fluids. Various ELISA assay systems, knowledgeable to those skilled in the art, can be used to accurately monitor the degree of perlecan in biological fluids as a potential diagnostic indicator and prognostic marker for patients during the progression of disease (i.e. monitoring of an amyloid disease for example). In addition, quantitative changes in perlecan autoantibody levels can also serve as a prognostic indicator monitoring how a live patient will respond to treatment which targets a given amyloid disease.

Other diagnostic methods utilizing the invention include diagnostic assays for measuring altered levels of perlecan, perlecan fragments, the ~220 kDa HSPG or ~220 kDa HSPG-fragments in various tissues compared to normal control tissue samples. Assays used to detect levels of perlecan, perlecan fragments, the ~220 kDa HSPG or ~220 kDa HSPG-fragments in a sample derived from a host are otherwise well-known to those skilled in the art and included radioimmunoassays, competitive-binding assays, Western blot analysis and preferably ELISA assays (as described above).

Yet another aspect of the present invention is to use the antibodies recognizing perlecan, perlecan fragments, the ~220 kDa HSPG or ~220 kDa HSPG-fragments for labelings, for example, with a radionucleotide, for radioimaging or radioguided surgery, for in vivo diagnosis, and/or for in vitro diagnosis. In one preferred embodiment, radiolabeled antibodies made (by one skilled in the art) against perlecan, perlecan fragments, the ~220 kDa HSPG or ~220 kDa HSPG-fragments may be used as minimally invasive techniques to locate perlecan, perlecan fragments, the ~220 kDa HSPG or ~220 kDa HSPG-fragments and concurrent amyloid deposits in a living patient. These same imaging techniques could then be used at regular intervals (i.e. every 6 months) to monitor the progression of the amyloid disease by following the specific levels of perlecan, perlecan fragments, the ~220 kDa HSPG or ~220 kDa HSPG-fragments.

Therapeutic Applications

Use of Perlecan, ~220 kDa HSPG and/or Antibodies

Yet another aspect of the present invention is to make use of clean perlecan, perlecan fragments, the ~220 kDa HSPG or ~220 kDa HSPG-fragments thereof The perlecan, perlecan fragments, ~220 kDa HSPG or ~220 kDa HSPG-fragments thereof can be used as potential blocking therapeutics for the interaction of perlecan, perlecan fragments, the ~220 kDa HSPG or ~220 kDa HSPG-fragments in a number of biological processes and diseases (such as in the amyloid diseases described above). In a preferred embodiment, perlecan, perlecan fragments, the ~220 kDa HSPG or ~220 kDa HSPG-fragments thereof may be used to block the interaction of perlecan, perlecan fragments, the ~220 kDa HSPG or ~220 kDa HSPG-fragments with a given target (i.e. amyloid deposits). Inhibition by clean perlecan, perlecan fragments, the ~220 kDa HSPG or ~220 kDa HSPG-fragments may alleviate the continued amyloid formation, deposition, accumulation and/or persistence observed in a given patient. Likewise, in another preferred embodiment antibodies made against perlecan, perlecan fragments, the ~220 kDa HSPG or ~220 kDa HSPG-fragments thereof (as described above) may be given to a human patient as potential blocking antibodies to disrupt continued amyloid formation, deposition, accumulation and/or persistence in the given patient.

Preparations of clean perlecan, perlecan fragments, the ~220 kDa HSPG or ~220 kDa HSPG-fragments for parenteral administration include sterile aqueous or non-aqueous solutions, suspensions, and emulsions, which may contain axillary agents or excipients which are known in the art. Pharmaceutical compositions such as tablets, pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, sterile packaged powders, can be prepared according to routine methods and are known in the art.

In yet another aspect of the invention, clean perlecan, perlecan fragments, the ~220 kDa HSPG or ~220 kDa HSPG-fragments may be used as an effective therapy to block amyloid formation, deposition, accumulation and/or persistence as observed in the amyloid diseases. For example, the invention includes a pharmaceutical composition for use in the treatment of amyloidoses comprising a pharmaceutically effective amount of a clean perlecan, perlecan fragment, ~220 kDa HSPG or ~220 kDa HSPG-fragment anti-idiotypic antibody and a pharmaceutically acceptable carrier. The compositions may contain the perlecan, perlecan fragment, ~220 kDa HSPG or ~220 kDa HSPG-fragment anti-idiotypic antibody, either unmodified, conjugated to a potentially therapeutic compound, conjugated to a second protein or protein portion or in a recombinant form (i.e. chimeric or bispecific perlecan, perlecan fragment, ~220 kDa HSPG or ~220 kDa HSPG-fragment antibody). The compositions may additionally include other antibodies or conjugates. The antibody compositions of the invention can be administered using conventional modes of administration including, but not limited to, topical, intravenous, intra-arterial, intraperitoneal, oral, intralymphatic, intramuscular or intralumbar. Intravenous administration is preferred. The compositions of the invention can be a variety of dosage forms, with the preferred form depending upon the mode of administration and the therapeutic application. Optimal dosage and modes of administration for all individual patient can readily be determined by conventional protocols.

Perlecan, perlecan fragments, the ~220 kDa HSPG or ~220 kDa HSPG-fragments, or antibodies of the present invention may be administered by any means that achieve their intended purpose, for example, to treat perlecan or ~220 kDa HSPG involved pathologies, such as Alzheimer's disease and other amyloid diseases, or other related pathologies, using a perlecan-derived or ~220 kDa HSPG-derived fragments as described herein, in the form of a pharmaceutical composition.

For example, administration of such a composition may be by various parenteral routes such as subcutaneous, intravenous, intradermal, intramuscular, intraperitoneal, intranasal, transdermal or buccal routes. Alternatively, or concurrently, administration may be by the oral route. Parenteral administration can be by bolus injection or by gradual perfusion over time.

A preferred mode of using a perlecan, perlecan fragment, ~220 kDa HSPG or ~220 kDa HSPG-fragment, or antibody pharmaceutical composition of the present invention is by oral administration or intravenous application.

A typical regimen for preventing, suppressing or treating perlecan-involved pathologies, such as Alzheimer's disease amyloidosis, comprises administration of an effective amount of clean perlecan, perlecan fragment, ~220 kDa HSPG or ~220 kDa HSPG-fragment-derived polypeptides, administered over a period of one or several days, up to and including between one week and about 24 months.

It is understood that the dosage of the clean perlecan, perlecan fragment, ~220 kDa HSPG or ~220 kDa HSPG-fragment of the present invention administered in vivo or in vitro will be dependent upon the age, sex, health, and weight of the recipient, kind of concurrent treatment, if any, frequency of treatment, and the nature of the effect desired. The most preferred dosage will be tailored to the individual subject, as is understood and determinable by one of skill in the art, without undue experimentation.

The total dose required for each treatment may be administered by multiple doses or in a single dose. A clean perlecan, perlecan fragment, ~220 kDa HSPG or ~220 kDa HSPG-fragment may be administered alone or in conjunction with other therapeutics directed to perlecan or ~220 kDa HSPG-involved pathologies, such as Alzheimer's disease or amyloid diseases, as described herein.

Effective amounts of a clean perlecan, perlecan fragment, ~220 kDa HSPG or ~220 kDa HSPG-fragment or composition, which may also include a perlecan, perlecan fragment, ~220 kDa HSPG or ~220 kDa HSPG-fragment derived antibody, are about 0.01 g to about 100 mg/kg body weight, and preferably from about 10 µg to about 50 mg/kg body weight, such as 0.05, 0.07, 0.09, 0.1, 0.5, 0.7, 0.9., 1, 2, 5, 10, 20, 25, 30, 40, 45, 50, 55, 60, 65, 70, 75, 80, 85, 90, 95 or 100 mg/kg.

Preparations for parenteral administration include sterile aqueous or non-aqueous solutions, suspensions, and emulsions, which may contain axillary agents or excipients which are known in the art. Pharmaceutical compositions comprising at least one perlecan, perlecan fragment, ~220 kDa HSPG or ~220 kDa HSPG-fragment, such as 1–10 or 1, 2, 3, 4, 5, 6, 7, 8, 9, or 10 perlecan, perlecan fragments, ~220 kDa HSPG or ~220 kDa HSPG-fragments, of the present invention may include all compositions wherein the perlecan, perlecan fragments, ~220 kDa HSPG or ~220 kDa HSPG-fragments is contained in an amount effective to achieve its intended purpose. In addition to at least one clean perlecan, perlecan fragment, ~220 kDa HSPG or ~220 kDa HSPG-fragments, a pharmaceutical composition may contain suitable pharmaceutically acceptable carriers, such as excipients, carriers and/or axillaries which facilitate processing of the active compounds into preparations which can be used pharmaceutically.

Pharmaceutical compositions comprising at least one clean perlecan, perlecan fragment, ~220 kDa HSPG or ~220 kDa HSPG-fragment or antibody may also include suitable solutions for administration intravenously, subcutaneously, dermally, orally, mucosally, rectally or may by injection or orally, and contain from about 0.01 to 99 percent, preferably about 20 to 75 percent of active component (i.e. polypeptide or antibody) together with the excipient. Pharmaceutical compositions for oral administration include pills, tablets, caplets, soft and hard gelatin capsules, lozenges, sachets, cachets, vegicaps, liquid drops, elixers, suspensions, emulsions, solutions, and syrups.

The clean perlecan, perlecan fragment, ~220 kDa HSPG or ~220 kDa HSPG-fragment for Alzheimer's disease and other central nervous system amyloidoses may be optimized to cross the blood-brain barrier. Methods of introductions include but are not limited to systemic administration, parenteral administration, i.e. via an intraperitoneal, intravenous, perioral, subcutaneous, intramuscular, intraarterial, intradermal, intramuscular, intranasal, epidural and oral routes. In a preferred embodiment, perlecan, perlecan fragments, the ~220 kDa HSPG or ~220 kDa HSPG-fragments may be directly administered to the cerebrospinal fluid by intraventricular injection. In a specific embodiment, it may be desirable to administer perlecan, perlecan fragments, the ~220 kDa HSPG or ~220 kDa HSPG-fragments locally to the area or tissue in need of treatment; this may be achieved by, for example, and not by way of limitation, local infusion during surgery, topical application, by injection, by infusion using a cannulae with osmotic pump, by means of a catheter, by means of a suppository, or by means of an implant.

In yet another embodiment, clean perlecan, perlecan fragments, the ~220 kDa HSPG or ~220 kDa HSPG-fragments may be delivered in a controlled release system, such as an osmotic pump. In yet another embodiment, a controlled release system can be placed in proximity to the therapeutic target, ie. the brain, thus requiring only a fraction of the systemic dose.

In yet another aspect of the present invention, peptidomimetic compounds modeled from clean perlecan, perlecan fragments, the ~220 kDa HSPG or ~220 kDa HSPG-fragments identified as binding Aβ or other amyloid proteins, may serve as potent inhibitors of amyloid formation, deposition, accumulation and/or persistence in Alzheimer's disease and other amyloidoses. Peptidomimetic modeling is implemented by standard procedures known to those skilled in the art.

Recombinant DNA technology, including human gene therapy, has direct applicability to perlecan, perlecan fragments, the ~220 kDa HSPG or ~220 kDa HSPG-fragments, of this invention. One skilled in the art can take peptide sequences from these molecules and create corresponding nucleotide sequences that code for the corresponding peptide sequences. These sequences can be cloned into vectors such as retroviral vectors, and the like. These vectors can, in turn, be transfected into human cells such as hepatocytes or fibroblasts, and the like. Such transfected cells can be introduced into humans to treat amyloid diseases. Alternatively, the genes can be introduced into the patients directly. The basic techniques of recombinant DNA technology are known to those of ordinary skill in the art and are disclosed in *Recombinant DNA* Second Edition, Watson, et al., W.H. Freeman and Company, New York, 1992, which is hereby incorporated by reference.

In yet another aspect of the present invention is to use anti-idiotypic antibodies to perlecan, perlecan fragments, the ~220 kDa HSPG or ~220 kDa HSPG-fragments as potent inhibitors of amyloid formation, deposition, accumulation and/or persistence in Alzheimer's disease and other amyloidoses. Production of anti-idiotypic antibodies is implemented by standard procedures knowledgeable to those skilled in the art.

Use of the Perlecan Product for Production of New Animal Models

Infusion Models for Alzheimer's Disease and Down's Syndrome Amyloidosis

The production of "clean" perlecan or the ~220 kDa HSPG product as described in the present invention can also be used to produce new animal models of the amyloidoses. For example, as a new model of Alzheimer's disease amyloidosis, perlecan, perlecan fragments, the ~220 kDa HSPG or ~220 kDa HSPG-fragments can be continuously infused in combination with beta-amyloid protein (Aβ) into the hippocampus of groups of rats or mice (as described in detail in section 7.1.1 and 7.1.2. In a preferred embodiment perlecan, perlecan fragments, the ~220 kDa HSPG or ~220 kDa HSPG-fragments (25 μg) is dissolved in water in a microcentrifuge tube containing 50 μg of Aβ (1–40) or (1–42). Using the described methods of Snow et al (*Neuron* 12:219–234, 1994) herewith incorporated by reference, perlecan, perlecan fragments, the ~220 kDa HSPG or ~220 kDa HSPG-fragments plus Aβ is continuously infused for 1 week into hippocampus (via stereotaxic surgeries knowledgeable by one skilled in the art) of groups (usually 10) of 3 month old Sprague-Dawley rats. Following the 1 week infusion the animals are sacrificed and the brains are removed as described in Snow et al (*Neuron* 12:219–234, 1994), and 6–8 μm serial sections spanning through the entire infusion site are cut from paraffin embedded blocks or from frozen sections. The extent of amyloid deposition per animal is then detected by Congo red staining (as viewed under polarized light) or Thioflavin S fluorescence and quantitated in a blind study using an arbitrary scoring method as described by Snow et al (*Neuron* 12:219–234, 1994). The use of perlecan, perlecan fragments, the ~220 kDa HSPG or ~220 kDa HSPG-fragments in this model can be used as a rapid model of fibrillar Aβ amyloid deposition, accumulation and persistence in vivo. In addition, this model may be used to rapidly screen potential therapeutics targeting fibrillar Aβ amyloid formation, deposition, accumulation and/or persistence. In a preferred embodiment, perlecan, perlecan fragments, the ~220 kDa HSPG or ~220 kDa HSPG-fragments plus Aβ plus therapeutic compound is directly infused into the hippocampus (as described above) of a group of animals and comparisons are made to a group of animals infused with only perlecan, perlecan fragments, the ~220 kDa HSPG or ~220 kDa HSPG-fragments plus Aβ. Compounds or drugs found to reduce amyloid formation, deposition, accumulation and/or persistence (as determined by Congo red or Thioflavin S scoring) in vivo are then identified as having potential therapeutic value.

In another preferred embodiment, the potentially therapeutic compound can be tested to reduce amyloid persistence over prolonged periods of time. In this model, groups of animals (usually 10 animals per group) are infused with perlecan, perlecan fragments, the ~220 kDa HSPG or ~220 kDa HSPG-fragments plus Aβ plus therapeutic compound and directly compared to groups of animals (usually 10 animals per group) infused with perlecan, perlecan fragments, the ~220 kDa HSPG or ~220 kDa HSPG-fragments plus Aβ. Following a 1 week infusion (as described above), the cannulae are removed with the animals under anesthesia, and the animals are then allowed to recover until sacrifice 1, 3, 6 or 12 months later. Serial sections are cut and amyloid is scored as described above. It is believed that persistent amyloid deposits can be observed in animals infused with perlecan, perlecan fragments, the ~220 kDa HSPG or ~220 kDa HSPG-fragments plus Aβ. Potent therapeutic compounds will be those that effectively reduce the amount of amyloid observed in comparison to those animals not given the therapeutic compound. These compounds can therefore be referred to as compounds which effectively reduce amyloid persistence in vivo.

In yet another preferred embodiment, potentially therapeutic compounds can be tested for reducing or eliminating pre-formed amyloid deposits. In this model, two groups of animals (usually 10 animals per group) are infused with perlecan, perlecan fragments, the ~220 kDa HSPG or ~220 kDa HSPG-fragments plus Aβ. Following a 1 week infusion (as described above), the cannulae and osmotic pumps are changed (with the animals under anesthesia), and a new (cannulae connected by vinyl tubing to a new osmotic pump, contains either vehicle only (i.e. double distilled water) or the potential therapeutic compound. Following a 1 week continuous infusion of either the vehicle or the potential therapeutic compound of interest, the animals are sacrificed. Serial sections are then cut through the entire infusion site and the extent of amyloid is measured by arbitrary blind scoring as described above. Potent therapeutic compounds will be those that are able to effectively remove pre-formed amyloid deposits. It is anticipated that little to no reduction in the amount of amyloid will be observed in the group of animals infused with vehicle only. These compounds can therefore be referred to as therapeutic compounds which effectively reduce pre-formed amyloid deposits in vivo.

New Animal Models of AA Amyloidosis

The consistent and reliable production of "clean" perlecan or the ~220 kDa HSPG as described in the present invention can also be used to produce a new animal model of AA amyloidosis. For example, perlecan, perlecan fragments, the ~220 kDa HSPG or ~220 kDa HSPG-fragments can be continuously infused into systemic organs (i.e. kidney, liver, spleen, lung or heart) or injected daily into the tail veins of rats or mice, in combination with AA amyloid protein. In a preferred embodiment perlecan, perlecan fragments, the ~220 kDa HSPG or ~220 kDa HSPG-fragments are dissolved in water in a microcentrifuge tube containing AA amyloid protein. Using the described methods of Snow et al (*Neuron* 12:219–234, 1994), perlecan, perlecan fragments, the ~220 kDa HSPG or ~220 kDa HSPG-fragments plus AA amyloid is continuously infused for 1 week into a systemic organ of choice (via stereotaxic surgeries knowledgeable by one skilled in the art) of groups (usually 10) of adult rats or mice. Alternatively, AA amyloid protein +/− perlecan, perlecan fragments, the ~220 kDa HSPG or ~220 kDa HSPG-fragments are injected daily into the tail veins of a group of rats or mice. Following the 1 week experimental period, the animals are sacrificed and the systemic organs are removed, and 6–8 μm serial sections are cut from paraffin embedded blocks or from frozen sections containing the tissues of interest. The extent of amyloid deposition in each tissue per animal is then detected by Congo red staining (as viewed under polarized light) or Thioflavin S fluorescence and quantitated in a blind study using an arbitrary scoring method as described by Snow et al (*Neuron* 12:219–234, 1994). The use of perlecan, perlecan fragments, the ~220 kDa HSPG or ~220 kDa HSPG-fragments in this model can be, used as a rapid model of fibrillar AA amyloid deposition, accumulation and persistence in vivo. In addition, this model may be used to rapidly screen potential therapeutics targeting AA amyloid formation, deposition, accumulation and/or persistence. In a preferred embodiment, perlecan, perlecan fragments, the ~220 kDa HSPG or ~220 kDa HSPG-fragments plus AA amyloid plus therapeutic compound is directly infused or injected (as described above) into a group of animals and comparisons are made to a group of animals infused or injected with only perlecan, perlecan fragments, the ~220 kDa HSPG or ~220 kDa HSPG-fragments plus Aβ. Compounds or drugs found to reduce amyloid formation, deposition, accumulation and/or persistence (as determined by Congo red or Thioflavin S scoring) in vivo are then identified as having potential therapeutic value.

New Animal Models of AL Amyloidosis

The consistent and reliable production of "clean" perlecan or the ~220 kDa HSPG as described in the present invention can also be used to produce a new animal model of AL amyloidosis. For example, perlecan, perlecan fragments, the ~220 kDa HSPG or ~220 kDa HSPG-fragments can be continuously infused into systemic organs (i.e. kidney, liver, spleen, lung or heart) or injected daily into the tail veins of rats or mice, in combination with AL amyloid protein. In a preferred embodiment perlecan, perlecan fragments, the ~220 kDa HSPG or ~220 kDa HSPG-fragments are dissolved in water in a microcentrifuge tube containing AL amyloid protein. Using the described methods of Snow et al (*Neuron* 12:219–234, 1994), perlecan, perlecan fragments, the ~220 kDa HSPG or ~220 kDa HSPG-fragments plus AL amyloid is continuously infused for 1 week into a systemic organ of choice (via stereotaxic surgeries knowledgeable by one skilled in the art) of groups (usually 10) of adult rats or mice. Alternatively, AL amyloid protein +/− perlecan, perlecan fragments, the ~220 kDa HSPG or ~220 kDa HSPG-fragments are injected daily into the tail veins of a group of rats or mice. Following the 1 week experimental period, the animals are sacrificed and the systemic organs are removed, and 6–8 μm serial sections are cut from paraffin embedded blocks or from frozen sections containing the tissues of interest. The extent of amyloid deposition in each tissue per animal is then detected by Congo red staining (as viewed under polarized light) or Thioflavin S fluorescence and quantitated in a blind study using an arbitrary scoring method as described by Snow et al (*Neuron* 12:219–234, 1994). The use of perlecan, perlecan fragments, the ~220 kDa HSPG or ~220 kDa HSPG-fragments in this model can be used as a rapid model of fibrillar AL amyloid deposition, accumulation and persistence in vivo. In addition, this model may be used to rapidly screen potential therapeutics targeting AL amyloid formation, deposition, accumulation and/or persistence. In a preferred embodiment, perlecan, perlecan fragments, the ~220 kDa HSPG or ~220 kDa HSPG-fragments plus AL amyloid plus therapeutic compound are directly infused or injected (as described above) into a group of animals and comparisons are made to a group of animals infused or injected with only perlecan, perlecan fragments, the ~220 kDa HSPG or ~220 kDa HSPG-fragments plus AL amyloid. Compounds or drugs found to reduce amyloid formation, deposition, accumulation and/or persistence (as determined by Congo red or Thioflavin S scoring) in vivo are then identified as having potential therapeutic value.

New Animal Models of Transthyretin/Prealbumin Amyloidosis

The consistent and reliable production of "clean" perlecan or the ~220 kDa HSPG as described in the present invention can also be used to produce a new animal model of transthyretin/prealbumin amyloidosis. For example, perlecan, perlecan fragments, the ~220 kDa HSPG or ~220 kDa HSPG-fragments can be continuously infused or injected daily into the sciatic nerve, dorsal root ganglion or autonomic ganglion of rats or mice, in combination with various normal or mutated transthyretin/prealbumin proteins. In a preferred embodiment perlecan, perlecan fragments, the ~220 kDa HSPG or ~220 kDa HSPG-fragments are dissolved in water in a microcentrifuge tube containing of normal or mutated transthyretin/prealbumin proteins. Using the described methods of Snow et al (*Neuron* 12:219–234, 1994), the perlecan, perlecan fragments, the ~220 kDa HSPG or ~220 kDa HSPG-fragments plus normal or mutated transthyretin/prealbumin amyloid are continuously infused for 1 week into sciatic nerve, dorsal root ganglion or autonomic ganglion (via stereotaxic surgeries knowledgeable by one skilled in the art) of groups (usually 10) of adult rats or mice. Alternatively, normal or mutated transthyretin/prealbumin +/− perlecan, perlecan fragments, the ~220 kDa HSPG or ~220 kDa HSPG-fragments are injected daily into sciatic nerve, dorsal root ganglion or autonomic ganglion of a group of rats or mice. Following the 1 week experimental period, the animals are sacrificed and the pertinent tissues are removed, and 6–8 μm serial sections are cut from paraffin embedded blocks or from frozen sections containing the tissues of interest. The extent of amyloid deposition in each tissue per animal is then detected by Congo red staining (as viewed under polarized light) or Thioflavin S fluorescence and quantitated in a blind study using an arbitrary scoring method as described by Snow et al (*Neuron* 12:219–234, 1994). The use of perlecan, perlecan fragments, the ~220 kDa HSPG or ~220 kDa HSPG-fragments in this model can be used as a rapid model of fibrillar transthyretin/prealbumin amyloid deposition, accumulation and persistence in vivo. In addition, this model may be used to rapidly screen potential therapeutics targeting transthyretin/prealbumin amyloid formation, deposition, accumulation and/or persistence. In a preferred embodiment, perlecan, perlecan fragments, the ~220 kDa HSPG or ~220 kDa HSPG-fragments plus normal or mutated transthyretin/prealbumin plus therapeutic compound are directly infused or injected (as described above) into a group of animals and comparisons are made to a group of animals infused or injected with only perlecan, perlecan fragments, the ~220 kDa HSPG or ~220 kDa HSPG-fragments plus normal or mutated transthyretin/prealbumin. Compounds or drugs found to reduce amyloid formation, deposition, accumulation and/or persistence (as determined by Congo red or Thioflavin S scoring) in vivo are then identified as having potential therapeutic value.

New Animal Models of Beta$_2$-Microglobulin Amyloidosis

The consistent and reliable production of "clean" perlecan or the ~220 kDa HSPG as described in the present invention can also be used to produce a new animal model of beta$_2$-microglobulin amyloidosis. For example, perlecan, perlecan fragments, the ~220 kDa HSPG or ~220 kDa HSPG-fragments can be continuously infused into the bloodstream (for example, through external jugular vein to superior vena cava) or injected daily into the tendon or hind leg (adjacent to the medial nerve) of rats or mice, in combination with beta$_2$-microglobulin. In a preferred embodiment perlecan, perlecan fragments, the ~220 kDa HSPG or ~220 kDa HSPG-fragments are dissolved in water in a microcentrifuge tube containing beta$_2$-microglobulin. Using the described methods of Snow et al (*Neuron* 12:219–234, 1994), the perlecan, perlecan fragments, the ~220 kDa HSPG or ~220 kDa HSPG-fragments plus beta$_2$-microglobulin are continuously infused for 1 week into the bloodstream (via stereotaxic surgeries knowledgeable by one skilled in the art) of groups (usually 10) of adult rats or mice. Alternatively, beta$_2$-microglobulin +/− perlecan, perlecan fragments, the ~220 kDa HSPG or ~220 kDa HSPG-fragments are injected daily into the tendon or hind leg of a group of rats or mice. Following the 1 week experimental period, the animals are sacrificed and the pertinent tissues are removed, and 6–8 μm serial sections are cut from paraffin embedded blocks or from frozen sections containing the tissues of interest. The extent of amyloid deposition in each tissue per animal is then detected by Congo red staining (as viewed under polarized light) or Thioflavin S fluorescence and quantitated in a blind study using an arbitrary scoring method as described by Snow et al (*Neuron* 12:219–234, 1994). The use of perlecan, perlecan fragments, the ~220 kDa HSPG or ~220 kDa HSPG-fragments in this model can be used as a rapid model of beta$_2$-microglobulin amyloid deposition, accumulation and persistence in vivo. In addition, this model may be used to rapidly screen potential therapeutics targeting beta$_2$-microglobulin amyloid formation, deposition, accumulation and/or persistence. In a preferred embodiment, perlecan, perlecan fragments, the ~220 kDa HSPG or ~220 kDa HSPG-fragments plus beta$_2$-microglobulin plus therapeutic compound is directly infused or injected (as described above) into a group of animals and comparisons are made to a group of animals infused or injected with only perlecan, perlecan fragments, the ~220 kDa HSPG or ~220 kDa HSPG-fragments plus beta$_2$-microglobulin. Compounds or drugs found to reduce amyloid formation, deposition, accumulation and/or persistence (as determined by Congo red or Thioflavin S scoring) in vivo are then identified as having potential therapeutic value.

New Animal Models of Amylin (Islet Amyloid Polypeptide) Amyloidosis

The consistent and reliable production of "clean" perlecan or the ~220 kDa HSPG as described in the present invention can also be used to produce a new animal model of amylin (islet amyloid polypeptide) amyloidosis. For example, perlecan, perlecan fragments, the ~220 kDa HSPG or ~220 kDa HSPG-fragments can be continuously infused or daily injected into the pancreas or bloodstream of rats or mice, in combination with human amylin. In a preferred embodiment perlecan, perlecan fragments, the ~220 kDa HSPG or ~220 kDa HSPG-fragments are dissolved in water in a microcentrifuge tube containing amylin. Using the described methods of Snow et al (*Neuron* 12:219–234, 1994), perlecan, perlecan fragments, the ~220 kDa HSPG or ~220 kDa HSPG-fragments plus amylin are continuously infused or daily injected for 1 week into the pancreas or bloodstream (via stereotaxic surgeries knowledgeable by one skilled in the art) of groups (usually 10) of adult rats or mice. Following the 1 week experimental period, the animals are sacrificed and the pancreas is removed, and 6–8 μm serial sections are cut from paraffin embedded blocks or from frozen sections containing the pancreas. The extent of amyloid deposition in the pancreas per animal is then detected by Congo red staining (as viewed under polarized light) or Thioflavin S fluorescence and quantitated in a blind study using an arbitrary scoring method as described by Snow et al (*Neuron* 12:219–234, 1994). The use of perlecan, perlecan fragments, the ~220 kDa HSPG or ~220 kDa HSPG-fragments in this model can be used as a rapid model of amylin (islet amyloid) deposition, accumulation and persistence in vivo. In addition, this model may be used to rapidly screen potential therapeutics targeting amylin (islet amyloid) formation, deposition, accumulation and/or persistence. In a preferred embodiment, perlecan, perlecan fragments, the ~220 kDa HSPG or ~220 kDa HSPG-fragments plus amylin plus therapeutic compound is directly infused or injected (as described above) into a group of animals and comparisons are made to a group of animals infused or injected with only perlecan, perlecan fragments, the ~220 kDa HSPG or ~220 kDa HSPG-fragments plus amylin. Compounds or drugs found to reduce amyloid formation, deposition, accumulation and/or persistence (as determined by Congo red or Thioflavin S scoring) in vivo are then identified as having potential therapeutic value.

New Animal Models of Endocrine Type Amyloidosis

The consistent and reliable production of "clean" perlecan or the ~220 kDa HSPG as described in the present invention can also be used to produce a new animal model of endocrine amyloidosis, such as observed when a variant of calcitonin is found in the amyloid of medullary carcinoma of the thyroid, as well as in the islets of Langerhans in the pancreas of patients with type II (non-insulin dependent) diabetes. For example, perlecan, perlecan fragments, the ~220 kDa HSPG or ~220 kDa HSPG-fragments can be continuously infused or daily injected into the thyroid gland or pancreas of rats or mice, in combination with calcitonin. In a preferred embodiment perlecan, perlecan fragments, the ~220 kDa HSPG or ~220 kDa HSPG-fragments are dissolved in water in a microcentrifuge tube containing calcitonin. Using the described methods of Snow et al (*Neuron* 12:219–234, 1994), perlecan, perlecan fragments, the ~220 kDa HSPG or ~220 kDa HSPG-fragments plus calcitonin are continuously infused or daily injected for 1 week into the thyroid gland or pancreas (via stereotaxic surgeries knowledgeable by one skilled in the art) of groups (usually 10) of adult rats or mice. Following the 1 week experimental period, the animals are sacrificed and the thyroid gland or pancreas is removed, and 6–8 μm serial sections are cut from paraffin embedded blocks or from frozen sections containing the thyroid gland or pancreas. The extent of amyloid deposition in the thyroid gland or pancreas per animal is then detected by Congo red staining (as viewed under polarized light) or Thioflavin S fluorescence and quantitated in a blind study using an arbitrary scoring method as described by Snow et al (*Neuron* 12:219–234, 1994). The use of perlecan, perlecan fragments, the ~220 kDa HSPG or ~220 kDa HSPG-fragments in this model can be used as a rapid model of endocrine amyloid deposition, accumulation and persistence in vivo. In addition, this model may be used to rapidly screen potential therapeutics targeting endocrine amyloid formation, deposition, accumulation and/or persistence. In a preferred embodiment, perlecan, perlecan fragments, the ~220 kDa HSPG or ~220 kDa HSPG-fragments plus calcitonin plus therapeutic compound is directly infused or injected (as described above) into a group of animals and comparisons are made to a group of animals infused or injected with only perlecan, perlecan fragments, the ~220 kDa HSPG or ~220 kDa HSPG-fragments plus calcitonin. Compounds or drugs found to reduce amyloid formation, deposition, accumulation and/or persistence (as determined by Congo red or Thioflavin S scoring) in vivo are then identified as having potential therapeutic value.

New Animal Models of Prion Protein Amyloidosis

The consistent and reliable production of "clean" perlecan or the ~220 kDa HSPG as described in the present invention can also be used to produce a new animal model of prion protein (PrP) amyloidosis. For example, perlecan, perlecan fragments, the ~220 kDa HSPG or ~220 kDa HSPG-fragments can be continuously infused in combination with PrP protein into the hippocampus of groups of rats or mice. In a preferred embodiment perlecan, perlecan fragments, the ~220 kDa HSPG or ~220 kDa HSPG-fragments are dissolved in water in a microcentrifuge tube containing PrP 27–30. Using the described methods of Snow et al (*Neuron* 12:219–234, 1994), perlecan, perlecan fragments, the ~220 kDa HSPG or ~220 kDa HSPG-fragments plus PrP are continuously infused for 1 week into hippocampus (via stereotaxic surgeries knowledgeable by one skilled in the art) of groups (usually 10) of adult rats or mice. Following the 1 week infusion the animals are sacrificed and the brains are removed as described in Snow et al (*Neuron* 12:219–234, 1994), and 6–8 µm serial sections spanning through the entire infusion site are cut from paraffin embedded blocks or from frozen sections. The extent of amyloid deposition per animal is then detected by Congo red staining (as viewed under polarized light) or Thioflavin S fluorescence and quantitated in a blind study using an arbitrary scoring method as described by Snow et al (*Neuron* 12:219–234, 1994). The use of perlecan, perlecan fragments, the ~220 kDa HSPG or ~220 kDa HSPG-fragments in this model can be used as a rapid model of PrP amyloid deposition, accumulation and persistence in vivo. In addition, this model may be used to rapidly screen potential therapeutics targeting PrP amyloid formation, deposition, accumulation and/or persistence. In a preferred embodiment, perlecan, perlecan fragments, the ~220 kDa HSPG or ~220 kDa HSPG-fragments plus PrP 27–30 plus therapeutic compound is directly infused into the hippocampus (as described above) of a group of animals and comparisons are made to a group of animals infused with only perlecan, perlecan fragments, the ~220 kDa HSPG or ~220 kDa HSPG-fragments plus PrP 27–30. Compounds or drugs found to reduce amyloid formation, deposition, accumulation and/or persistence (as determined by Congo red or Thioflavin S scoring) in vivo are then identified as having potential therapeutic value.

We claim:

1. A method of preparation of substantially pure perlecan from an extract source, the method comprising the following steps: a) isolation of an extracted perlecan by a first molecular sieve column chromatography, followed by b) running anion exchange column chromatography, followed by c) running a second molecular sieve column chromatography employing a Sephacryl S-1000 column.

2. The method of claim 1 wherein the extract source is Engelbreth-Holm-Swarm tumor tissue.

3. The method of claim 1 further comprising the step, after step c), of further isolation by a column containing immobilized glycosaminoglycans.

4. The method of claim 1 wherein the preparation proceeds to a level of contaminants in the substantially pure perlecan of less than 1% by weight.

5. The method of claim 1 wherein the preparation proceeds to a level of contamination by DNA in the substantially pure perlecan of less than 1% by weight.

6. The method of claim 4 wherein the isolation proceeds to a level of contaminants less than or equal to 0.1% by weight.

7. The method of claim 3 wherein the isolation by a column containing immobilized glycosaminoglycans employs a heparin-Sepharose column.

8. The method of claim 3 further comprising, after the step of isolation by a column containing immobilized glycosaminoglycans, the step of running a third molecular sieve column chromatography.

9. The method of claim 8 wherein the third molecular sieve column chromatography employs a Sephacryl S-1000 column.

10. A method of preparation of substantially pure perlecan from an extract source, the method comprising the following steps: a) isolation of an extracted perlecan by a first molecular sieve column chromatography employing a Sephacryl S-400 column, followed by b) running anion exchange column chromatography, followed by c) running a second molecular sieve column employing a Sephacryl S-1000 column.

11. A method of preparation of substantially pure perlecan from an extract source, the method comprising the following steps: a) isolation of an extracted perlecan by a first molecular sieve column chromatography employing a Sephacryl S-400 column, followed by b) running anion exchange column chromatography employing a DEAB-Sephacel column, followed by c) running a second molecular sieve column employing a Sephacryl S-1000 column.

12. A method of preparation of substantially pure perlecan from an extract source, the method comprising the following steps: a) isolation of an extracted perlecan by a first molecular sieve column chromatography, followed by b) running a sulphopropyl sepharose cation exchange column, followed by c) running anion exchange column chromatography, followed by d) running a second molecular sieve column chromatography to yield substantially pure perlecan.

13. A method of preparation of substantially pure perlecan from an extract source, the method comprising the following steps: a) isolation of an extracted perlecan by a first molecular sieve column chromatography, followed by b) running anion exchange column chromatography, followed by c) running a second molecular sieve column chromatography, followed by d) running a heparin-Sepharose column chromatography to yield substantially pure perlecan.

* * * * *

UNITED STATES PATENT AND TRADEMARK OFFICE
CERTIFICATE OF CORRECTION

PATENT NO.         : 7,094,580 B2                                                Page 1 of 1
APPLICATION NO. : 10/323323
DATED              : August 22, 2006
INVENTOR(S)        : Castillo et al.

It is certified that error appears in the above-identified patent and that said Letters Patent is hereby corrected as shown below:

Column 1, line 10, Insert

--This invention was made with US Government support under grant numbers AGO5136 and AG12953 awarded by the National Institutes of Health. The US Government has certain rights in this invention.--

Signed and Sealed this

Twenty-first Day of August, 2007

JON W. DUDAS
*Director of the United States Patent and Trademark Office*